(12) United States Patent
Dubray et al.

(10) Patent No.: US 11,498,890 B1
(45) Date of Patent: Nov. 15, 2022

(54) NON-OXIDATIVE CONVERSION OF METHANE INTO ETHYLENE USING ISOMORPHOUS METAL-SUBSTITUTED ZEOLITE FRAMEWORK CATALYST

(71) Applicants: TotalEnergies OneTech, Courbevoie (FR); CENTRE NATIONAL DE LA RECHERCHE SCIENTIFIQUE (CNRS), Paris (FR)

(72) Inventors: Florent Dubray, Caen (FR); Svetlana Mintova, Basly (FR); Jean-Pierre Gilson, Fouesnant (FR); Stanislav Konnov, Moscow (RU); Stijn Van Daele, Halle (BE); Nikolai Nesterenko, Nivelles (BE)

(73) Assignees: TOTALENERGIES ONETECH, Courbevoie (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 17/770,188

(22) PCT Filed: Oct. 26, 2020

(86) PCT No.: PCT/EP2020/080051
§ 371 (c)(1),
(2) Date: Apr. 19, 2022

(87) PCT Pub. No.: WO2021/083839
PCT Pub. Date: May 6, 2021

(30) Foreign Application Priority Data

Oct. 28, 2019  (EP) .................................. 19315132.1

(51) Int. Cl.
*C07C 2/76* (2006.01)
*C01B 39/40* (2006.01)
(Continued)

(52) U.S. Cl.
CPC ................. *C07C 2/76* (2013.01); *B01J 29/48* (2013.01); *C01B 37/005* (2013.01); *C01B 39/40* (2013.01);
(Continued)

(58) Field of Classification Search
CPC ......... C07C 2/76; C07C 2/84; C07C 2529/40; C07C 2529/48; B01J 29/48; B01J 37/005; B01J 39/40
See application file for complete search history.

(56) References Cited

U.S. PATENT DOCUMENTS 4,891,463 A * 1/1990 Chu .......................... C07C 5/41
585/417
2004/0192990 A1 * 9/2004 Choudhary ............... C07C 1/20
585/638
(Continued)

FOREIGN PATENT DOCUMENTS

CN   107537555 A    1/2018
CN   106914243 B   10/2019
(Continued)

OTHER PUBLICATIONS

S. Tolborg et al., "Incorporation of tin affects crystallization, morphology, and crystal composition of Sn-Beta†"; J. Mat. Chem. A., 2014, 2, 20252-20262.
(Continued)

*Primary Examiner* — Ali Z Fadhel
(74) *Attorney, Agent, or Firm* — Ewing & Jones, PLLC

(57) ABSTRACT

Process for the conversion of non-oxidative coupling of methane to ethylene, under non-oxidative conditions, comprising: providing a first stream containing at least 50 vol. % of methane based on the total volume of said first stream; providing a catalyst; putting in contact said first stream with said catalyst at a weight hour space velocity ranging from
(Continued)

0.5 to 100 h$^{-1}$, a temperature ranging from 500° C. to 1100° C. and a pressure ranging from 0.1 MPa to 5 Mpa in the absence of oxygen; recovering a second stream containing unconverted methane if any, ethylene and hydrocarbons having at least 2 carbon atoms. Said process is remarkable in that said catalyst is a synthetic zeolite material, containing at least one metal M with silicon to metal M molar ratio Si/M as determined by inductively coupled plasma optical emission spectrometry ranging from 100 to 65440 and in that said metal M is incorporated inside of the zeolite tetrahedral sites.

20 Claims, 11 Drawing Sheets

(51) Int. Cl.
B01J 29/48 (2006.01)
C01B 37/00 (2006.01)
C07C 2/84 (2006.01)
(52) U.S. Cl.
CPC ............ C07C 2/84 (2013.01); C07C 2529/40 (2013.01); C07C 2529/48 (2013.01)

(56) References Cited

U.S. PATENT DOCUMENTS

| | | | |
|---|---|---|---|
| 2014/0336432 A1* | 11/2014 | Bao | B01J 23/755 502/259 |
| 2016/0362351 A1 | 12/2016 | Nagaki | |
| 2018/0169621 A1* | 6/2018 | Bao | B01J 23/83 |
| 2018/0296974 A1* | 10/2018 | Wachsman | B01D 71/024 |
| 2019/0143288 A1* | 5/2019 | Bao | B01J 19/0013 585/636 |

FOREIGN PATENT DOCUMENTS

| | | |
|---|---|---|
| WO | 9733830 A1 | 9/1997 |
| WO | 2014/183337 A1 | 11/2014 |
| WO | 2015/018807 A2 | 2/2015 |
| WO | 2017/062663 A1 | 4/2017 |
| WO | 2017068387 A1 | 4/2017 |

OTHER PUBLICATIONS

N.P. Van Der Graaff et al., "Synthesis of Sn-Beta with Exclusive and High Framework Sn Content"; Chem. Cat. Chem., 2015, 10 pages.
N. Garcia Vargas et al., "Synthesis and characterization of tin(IV) MFI: Sodium inhibits the synthesis of phase pure materials"; Microporous and Mesoporous Materials, 152 (2012) 37-49.
Yong Sig Ko et al., "Synthesis and Characterization of Zirconium Silicalite-1"; Korean J. Chem. Eng. 15(4), 423-428 (1998).
International Search Report and Written Opinion issued in Application No. PCT/EP2020/080051, dated Jan. 12, 2021; 9 pages.
International Preliminary Report on Patentability issued in Application No. PCT/EP2020/080051, dated Oct. 5, 2021; 6 pages.
J. Grand et al., "One-pot synthesis of silanol-free nanosized MFI zeolite"; Nature Materials (2017) 16, 1010-1015.
F. Dubray et al., "Direct Evidence for Single Molybdenum Atoms Incorporated in the Framework of MFI Zeolite Nanocrystals"; J Am. Chem. Soc 141 (2019) 8689-8693.
Xiaoguang Guo et al., "Direct, Nonoxidative Conversion of Methane to Ethylene, Aromatics, and Hydrogen"; Science, 2014, 344, 616-619.
R.M. Barrer, "Hydrothermal Chemistry of Zeolites", 1982, Academic Press, London.
Ch. Baerlocher et al., "Atlas of Zeolite Framework Types", 6th revised edition, 2007, Elsevier.

* cited by examiner

NON-OXIDATIVE CONVERSION OF METHANE INTO ETHYLENE USING ISOMORPHOUS METAL-SUBSTITUTED ZEOLITE FRAMEWORK CATALYST

CROSS-REFERENCE TO RELATED APPLICATIONS

This application claims the benefit of PCT/EP2020/080051 filed Oct. 26, 2020, which claims priority from EP 19315132.1 filed Oct. 28, 2019, which are incorporated herein by reference in their entireties for all purposes.

TECHNICAL FIELD

The present disclosure relates to the conversion of methane into ethylene performed on a particular catalyst. In this particular catalyst, metals are introduced in the framework of the zeolite by isomorphous substitution. The catalyst can be prepared using two methods of preparation. The first method is based on a hydrothermal synthesis in which the metal addition to the precursor suspensions (gel) is delayed. This so-called "staged-synthesis method" allows obtaining nanosized highly homogeneous crystalline zeolite structures with control over the metal location. The second method is based on a hydrothermal reaction of the metal with the zeolite. This method allows for obtaining zeolite with control over the metal location.

TECHNICAL BACKGROUND

Large quantities of methane are available worldwide but they are difficult and costly to transport. Additionally, methane has a market value of fuel whereas other components such as ethylene have a higher value. Many attempts were made to convert methane into more valuable products or into products that are easier to transport.

Transformation of methane has been abundantly studied in the literature. In particular, the oxidative coupling of methane (OCM) was widely studied. However, the OCM process has several disadvantages. The selectivity of this reaction is relatively low due to the formation of CO and $CO_2$. Therefore, a reasonable selectivity to C2+ hydrocarbons could be reached only at low methane conversion. In the C2 fraction, a significant amount of ethane is produced in addition to ethylene, which makes separation process very costly. In addition to this, the OCM is also a highly exothermic reaction, which requires a high-temperature activation implying that it is necessary to have a catalyst with high thermal stability and means for heat management.

Consequently, other routes were studied to convert methane into ethylene. In particular, non-oxidative routes were considered by the various authors.

Xiaoguang Guo et al. (*Science*, 2014, 344, 616-619) describe the direct, non-oxidative conversion of $CH_4$ into $H_2$-ethylene and aromatics at high temperature (1363 K) with the help of a catalyst being lattice-confined single iron sites embedded within a silica matrix. The disadvantages of the process are the requirement of very high temperature and co-production of naphthalene and benzene.

US 2016/0362351 describes a method for producing C2+ hydrocarbons and $H_2$ comprising (a) introducing to a reactor a reactant mixture comprising methane, (b) heating the reactant mixture to a preheating temperature to yield a heated mixture, (c) generating free radicals in the heated mixture to form a primary effluent mixture comprising free radicals, C2+ hydrocarbons, $H_2$, and unreacted methane, (d) reacting the primary effluent mixture in a secondary reaction zone to form a secondary effluent mixture comprising C2+ hydrocarbons, $H_2$, free radicals, and unreacted methane, at a secondary reaction zone temperature that is greater than the preheating temperature, wherein a free radicals amount in the primary effluent mixture is greater than a free radicals amount in the secondary effluent mixture, (e) cooling the secondary effluent mixture to a quench temperature lower than the secondary reaction zone temperature to yield a product mixture comprising C2+ hydrocarbons and $H_2$, and (f) recovering the product mixture.

WO2014/183337 describes the preparation of a metal lattice-doping catalyst in an amorphous molten state. The process of converting methane into olefins, aromatics, and hydrogen using the catalyst under oxygen-free, continuous flowing conditions is also described. Under the conditions encountered in a fixed bed reactor (i.e. reaction temperature: 750-1200° C.; reaction pressure: atmospheric pressure; the weight hourly space velocity of feed gas: 1000-30000 ml/g/h; and fixed bed), the conversion of methane is 8-50%. The selectivity of olefins is 30-90%. And the selectivity of aromatics is 10-70%.

WO2017/062663 describes non-oxidative direct methane conversion (NDMC) to value-added products, such as $H_2$, C2 hydrocarbons, and aromatics, within a particular design. The reactor has a first volume, where a feed gas including methane is provided, separated from a second volume, where a sweep gas is provided, by a dense thin film membrane supported on a porous wall. The thin-film membrane is a mixed ionic-electronic permeable membrane that allows $H_2$ generated in the first volume to be transported to the second volume for removal by (or reaction with) the sweep gas. A catalyst can be provided in or adjacent to the first volume. The typical catalyst is metal-doped quartz material (e.g., $Fe/SiO_2$) or a metal/zeolite material (e.g., Mo/ZSM5).

WO2015/018807 describes a process for the oxygen-free conversion of methane to ethylene on zeolite catalysts and catalysts comprising a zeolite belonging to the groups AHT, -CHI, CZP, HEU, JRY, JST, LAU, LOV, NAB, MVY, RSN, STT, VSV, WEI, preferred RRO, a metal selected from the group consisting of Mo, Fe, Co, Ni, Cu, Ag, Mg, W, Re, Ga, Ru, Rh, Pd, Ir, Pt and mixtures thereof, preferably Mo.

The non-oxidative conversion of methane into ethylene is not fully optimized. The latter does hold high potential as a method to decarbonize natural gas to chemical products and hydrogen. There is still a need to find more active and selective catalysts. In particular, there is still a need to find selective catalyst allowing mainly to form C2 hydrocarbon fraction containing mainly ethylene. There is also still a need to have a catalyst stable with time. Zeolites are well-known crystalline catalysts that are widely used as a catalyst and offer high potential for this reaction.

Zeolites are structurally complex inorganic polymers with a three-dimensional crystalline skeleton of $TO_4$ tetrahedral. The centre of the tetrahedral is generally a silicon or aluminium atom, which corresponds to a $SiO_4$ and $AlO_4$ tetrahedron respectively. These tetrahedrals are connected by common oxygen atoms. The complete structure forms a three-dimensional network, exhibiting some micropores, cages and channels. They have a demonstrated track record in many applications such as catalysis, separation and ion exchange due to their unique properties of acidic molecular sieves. In the past decades, many efforts have been devoted to tuning zeolite properties such as acidity and redox potential to improve their performances. Such modification of zeolite acidity and redox properties is usually performed through the introduction of transition metal atoms. The resulting properties of the material will then highly depend on the nature of the metal species introduced in the zeolite, depending on itself on the way the metal was introduced in the first place.

Two main groups of metal species exist in zeolites: (i) non-framework metal species and (ii) framework metal species. Non-framework metal species are sitting in non-framework positions of the zeolite structure. On the other hand, framework metal stands for metal introduced in crystallographic tetrahedral positions from the zeolite framework thanks to a procedure called isomorphous substitution. Isomorphous substitution is a procedure allowing to replace one silicon atom from the zeolite framework with any other given elements.

Isomorphous substitution can be performed using two main approaches: (i) direct hydrothermal synthesis or (ii) post-synthesis approach. The direct synthesis approach (i) corresponds to the direct introduction of metal source within the precursor suspension (gel) before crystallization. The presence of metallic species in the precursors then allows replacing part of silica by other metals during the crystallization process, thus, achieving isomorphous substitution. However, the presence of metallic species in the precursor suspension (gel) is not to be considered lightly, as it can influence strongly the nucleation and crystallization process as described for the synthesis of Sn-BEA zeolite by S. Tolborg et al. (*J. Mat. Chem. A.*, 2014, 2, 20252-20262). Similarly, a lot of silanols can still be observed in Sn-BEA zeolite after Sn introduction in the work from van der Graaff N. P. W., et al. (*Chem. Cat. Chem.*, 2015, 7, 1152-1160).

N. Garcia Vargas et al. (*Microporous and Mesoporous Materials*, 2012, 152, 37-49) reported the preparation of tin (IV) MFI where the presence of sodium hydroxide makes it difficult to have a pure Sn-MFI material.

Yong Sig Ko et al. (*Korean J. Chem. Eng.*, 1998, 15(4), 423-428) reported the preparation of zirconium silicalite-1 (ZS-1) prepared via hydrothermal synthesis method where the zirconium precursor is incorporated directly into the zeolite precursor gel.

Similarly, WO2017/068387 reported a method for the preparation of nanosized synthetic zeolite wherein the metal is incorporated in a clear solution containing the other components of the zeolite i.e. before any crystallisation of the zeolite.

In WO97/33830 described the direct hydrothermal synthesis of zeolite Ti-Beta in absence of aluminium, using hydrofluoric acid (HF) in the absence of seeds, by hydrolyzing a mixture of tetraethyl orthosilicate, tetraethylammonium hydroxide, water, hydrogen peroxide; adding tetraethyl orthotitanate to the resulting suspension, and pursuing hydrolysis; evaporating off the ethanol; adding HF to the resulting mixture, and heating in an autoclave at 140° C. for 11 days. Such preparation of zeolite in the presence of fluoride anions leads to the formation of large crystals; the high toxicity of HF and the difficulties it brings when scaled-up have to be taken into consideration.

In CN 107 537 555, the methane anaerobic dehydrogenation aromatization reaction has been described in the presence of zeolite material with molybdenum as a catalyst for forming benzene and ethylene. The catalyst, Mo/HZSM-5, is prepared by contacting a first solution comprising the silicon precursor and the metal precursor with a second solution comprising the tetraalkylammonium hydroxide. This catalyst favours the formation of benzene.

In CN 106 914 243, the methane anaerobic production of ethylene in the presence of a molten amorphous material containing metal is described. The dispersion of the metal into the amorphous material is performed thanks to solid-phase doping techniques, such as improved chemical vapour deposition, sol-gel combined improved chemical vapour deposition or porous silicon compound infiltration combined with improved chemical vapour deposition. Besides ethylene, other compounds such as aromatic hydrocarbons and naphthalene are generated.

Many efforts were devoted to the reduction of crystal size to reduce diffusion limitations for catalysis applications with sometimes limited success. However, a catalyst with reduced crystal size is of particular interest for catalysis and reactions of conversion of methane into ethylene.

SUMMARY

The present disclosure aims to provide a simple and economic preparation process for converting methane into ethylene and hydrogen. This particular process is also remarkable in that a particular catalyst used.

The disclosure relates to a process for the conversion of methane into ethylene and hydrogen, under non-oxidative conditions, comprising the following steps:
i. providing a first stream containing at least 50 vol. % of methane based on the total volume of the first stream;
ii. providing a catalyst
iii. putting in contact the first stream with said catalyst at a weight hour space velocity ranging from 0.5 to 100 $h^{-1}$, at a temperature ranging from 800° C. to 1100° C. and at a pressure ranging from 0.1 MPa (1 bar) to 5.0 MPa (50 bar) in the absence of oxygen;
iv. recovering a second stream containing unconverted methane if any, ethylene and hydrocarbons having at least 2 carbon atoms, the process is remarkable in that said catalyst is a synthetic zeolite material, containing at least one metal M with silicon to metal M molar ratio Si/M ranging from 100 to 65440 as determined by inductively coupled plasma optical emission spectrometry and in that said metal M is incorporated inside of the zeolite tetrahedral sites (T-sites).

In other words, the metal M is incorporated in the framework of the zeolite.

With preference, one or more of the following embodiments can be used to better define the disclosed process:
The first stream comprises at least 50 ppm of sulfur-containing compounds.
The first stream comprises at least one water stream in an amount of at least 1 vol. % based on the total volume of the said first stream.
The first stream comprises at least 0.5 vol. % of $CO_2$ based on the total volume of the said first stream.
The temperature of step (iii) is at least 820° C., preferably at least 840° C. or at least 850° C.
The temperature of step (iii) ranges from 800° C. to 1000° C.; for example, from 820° C. to 950° C.; for example, from 840° C. to 900° C.
The pressure of step (iii) ranges from 0.1 MPa to 4.0 MPa (1 to 40 bar), preferably from 0.1 MPa to 2.0 MPa (1 to 20 bar).

In an embodiment, said catalyst is pre-treated at step (ii) with a third stream containing CO, $CO_2$, $C_2H_4$, $C_2H_6$, $H_2O$, C3+ hydrocarbon mixture containing at least 10 wt. % of acyclic hydrocarbons or a mixture of thereof. With preference, said catalyst is pre-treated at step (ii) at a temperature comprised between 450° C. and 850° C., more preferably at a temperature comprised between 650° C. and 750° C. Advantageously, said catalyst is pre-treated at step (ii) with a weight hour space velocity comprised between 0.1 h⁻¹ and 100 h⁻¹. In particular, said catalyst is pre-treated at step (ii) at a pressure between 0.1 MPa and 10 MPa.

In an embodiment, said catalyst is pre-treated at step (ii) with a third stream containing CO, $CO_2$, $C_2H_4$, $C_2H_6$, $H_2O$, C3+ hydrocarbon mixture containing at least 10 wt. % of acyclic hydrocarbons or a mixture of thereof; with preference, said catalyst is pre-treated at step (ii) at a temperature comprised between 450° C. and 850° C., and/or a weight hour space velocity comprised between 0.1 h⁻¹ and 100 h⁻¹, and/or at a pressure between 0.1 MPa and 10 MPa In an embodiment, said catalyst is pre-treated at step (ii) with a third stream containing CO, $CO_2$, $C_2H_4$, $C_2H_6$, $H_2O$, C3+ hydrocarbon mixture containing at least 10 wt. % of acyclic hydrocarbons or a mixture of thereof; at a temperature comprised between 450° C. and 750° C., a weight hour space velocity comprised between 0.1 h⁻¹ and 100 h⁻¹, and at a pressure between 0.1 MPa and 10 MPa.

In an embodiment, said synthetic zeolite material is selected from the group of MOR, MWW, EUO, TON, MTT, CHA, MEL, MFI, BEA and/or FAU families, preferably from the group of MWW, EUO, TON and/or MTT families, preferably from the group of MWW family. For example, a synthetic zeolite material selected from the MWW family is MCM-22. For example, a synthetic zeolite material selected from the EUO family is EU-1. For example, a synthetic zeolite material selected from the TON family is ZSM-22. For example, a synthetic zeolite material selected from the MTT family is ZSM-23.

With preference, one or more of the following embodiments can be used to better define the synthetic zeolite material used in the disclosed process.

Said synthetic zeolite material presents no silanol, preferably evidenced via Raman spectroscopy with the absence of a band in the range comprised between 970 cm⁻¹ and 990 cm⁻¹, in particular with the absence of a band at 980 cm⁻¹.

Said synthetic zeolite material comprises a content of 0.1 to 10 wt. % of metal M based on the total mass of the synthetic zeolite material measured according to EDS-TEM, preferably a content of 0.1 to 1.5 wt. %.

Said synthetic zeolite material has a specific surface area ranging from 300 to 500 m²/g measured according to the BET method ASTM D3663-03.

Said synthetic zeolite material has a pore volume from 0.1 to 0.7 cm³/g measured according to the BET method ASTM D3663-03.

Said synthetic zeolite material has an external surface area from 10 to 190 m²/g measured according to the BET method ASTM D3663-03, preferably from 20 to 190 m²/g.

Said synthetic zeolite material contains no aluminium or contains aluminium with a molar ratio Si/Al from 5 to 2000 as determined by inductively coupled plasma optical emission spectrometry, preferably from 10 to 2000, more preferably from 20 to 1000.

In an embodiment, said metal M is selected from Fe, W, V, Mo, Sn, Zr, Ag, Co, Ni, Cu, Ti, In, Zn and any mixture thereof, preferably selected from Fe, W, V, Mo, Sn, Zr, Ag, Ni, Cu, Ti and any mixture thereof, more preferably selected from Fe, W, V, Mo, Sn, Zr, Ag and any mixture thereof, even more preferably selected from Fe, W, V, Mo, Sn, and any mixture thereof, most preferably selected from V, Mo and any mixture thereof or said metal is Mo.

In a first embodiment, said synthetic zeolite material can preferably be prepared according to the following steps:
a) contacting at least one source of silicon, at least one tetra-alkylammonium hydroxide structure-directing agent (TAAOH) and water, so as to obtain an aqueous suspension having the following molar composition (I):

in which:
0.04<y<0.40, preferably 0.2<y<0.3,
8<z<120, preferably 20<z<50;
b) ageing during a time ranging between 1 h and 100 h the resulting aqueous suspension from step (a) at a temperature ranging from 10° C. to 50° C., so as to obtain an aged aqueous suspension;
c) heating for at least 30 min the aged aqueous suspension of step (b) at a temperature ranging from 40° C. to 180° C., so as to obtain a solution;
d) cooling the solution obtained at step (c) to 20° C., adding at least one source of alkali metal M' and at least one source of metal M, to obtain a gel having the molar composition (II):

in which: the M'/M ratio varies from 0.1 to 4,
0.04<y<0.40, preferably 0.2<y<0.3,
8<z<120, preferably 20<z<50,
0.0004<x<0.15, preferably 0.01<x<0.1,
0.0004<w<0.30, preferably 0.01<w<0.2,
n is an integer equal to 1 or 2, and/or
m is an integer and 1<m<6;
e) ageing said gel obtained at step (d) at a temperature ranging from 10° C. to 35° C. for at least 30 min;
f) heating the solution obtained at step (e) at a temperature ranging from 40° C. to 180° C., for at least 30 minutes and at most 96 h;
g) separating the solid from said liquid obtained at step (f);
h) calcining said solid obtained at step (g) to obtain said synthetic zeolite material.

Advantageously, during the preparation of said synthetic zeolite material, the incorporation of said metal inside of the zeolite T-sites increases the unit cell volume of at least 10% relative to the Al-containing sample as obtained by Le Bail profile refinement of the diffraction pattern determined by XRD.

The method of preparation of said synthetic zeolite material presents the advantage that the metal M suppresses the defects being the silanols and silanol nests. The defects are saturated with metal coordinated with 4 or 2 Si (T-atoms) with oxygen bridges depending on its coordination stage. Once saturated with the metals, said synthetic zeolite material presents useful properties such as hydrophobicity, colloidal stability, and thermal resistance.

The method of the present disclosure allows fine control of nucleation stage [steps (a) and (b)] in the absence of the metal M, and the absence of the crystallization steps [steps (c) and (f)]. Such control of the synthesis method allows to finely tune crystal size based on the enhanced control of the nucleation step. The possibility to conduct the nucleation step in absence of metal M at stage [steps (a) and (b)] prevents the interaction of said metal M at the nucleation stage. Consequently, the synthetic zeolite material obtained has a similar particle size, particle size distribution, and morphology as the purely-siliceous zeolite that would be obtained without steps (d), (e), and (f). As a consequence, the method does not require space confiners to limit the growth of crystals.

Additionally, without willing to be bound to any theory, it is believed that the method of the disclosure allows controlling the radial distribution of said metal M in the zeolitic material. The metal M is introduced in step (d) at an early stage of nucleation i.e. after the heating of step (c). In this case, the defects are homogeneously distributed in the material produced. This allows a homogeneous radial distribution of the metal M in the synthetic zeolite material.

The present method of preparation is also advantageous in that the starting materials used in the synthesis are those commonly used in the commercial production of zeolites. In comparison with the prior art, there is no need of a fluoride-based agent. This is particularly advantageous for practical and safety reasons. The method using an alkaline mediating agent instead of fluoride, the nucleation step is faster. This avoids the formation of large crystals that are otherwise formed when using fluoride mediating agent, where a slower nucleation rate is observed.

In a first alternative, said at least one source of an alkali metal M' and said at least one source of metal M originate from the same compound, with preference said at least one source of an alkali metal M' and said at least one source of metal M is a sodium or a potassium salt of the metal M. More preferably, said at least one source of an alkali metal M' and said at least one source of metal M originate from $Na_2WO_4.2H_2O$, $K_2WO_4$, $NaVO_3$, $KVO_3$, $Na_2MoO_4.2H_2O$, $K_2MoO_4$, $Na_2SnO_3.3H_2O$, $K_2SnO_3.3H_2O$, $Na_2ZrO_3$ or $K_2ZrO_3$.

In a second alternative, said at least one source of an alkali metal M' and said at least one source of metal M originate from two different compounds; with preference said at least one source of metal M is a salt soluble together with said at least one source of an alkali metal M' in water. More preferably, said at least one source of metal M is an ammonium salt, even more preferably $(NH_4)_6Mo_7O_{24}$.

With preference, whatever is the framework type of the synthetic zeolite material and whatever is the alternative chosen among the first alternative and the second alternative, one or more of the following features can be used to better define the preparation of said synthetic zeolite material as defined in the first embodiment:

Said at least one source of silicon of step (a) is selected from silica hydrogel, silicic acid, colloidal silica, fumed silica, tetraalkyl orthosilicates, silica hydroxides, precipitated silica and sodium silicates.

Said at least one tetraalkylammonium hydroxide structure-directing agent is tetraethylammonium hydroxide, tetrabutylammonium hydroxide or tetrapropylammonium hydroxide.

Step (b) is performed at a temperature ranging from 10° C. to 35° C.

Step (b) is carried out under stirring,

Step (b) is carried out during a time ranging between 10 h and 25 h, preferably between 17 h and 20 h.

Step (c) is performed at a temperature ranging from 60° C. to 120° C.

Step (c) is performed for at most 48 h, preferably for at most 12 h.

Step (c) is performed during a time comprised between 12 h and 48 h.

The gel obtained in said step (d) has a pH ranging from 9 to 14, preferably from 11 to 14.

The gel obtained in said step (d) is amorphous or composed of embryonic zeolite, or partially crystalline, or fully crystalline as measured by powdered XRD.

Said at least one source of alkali metal M' is selected from Li, Na, K, or Cs.

Step (e) is carried out under stirring,

Step (e) is carried out during a time ranging between 10 h and 25 h, preferably between 17 h and 20 h.

Step (f) is performed at a temperature ranging between 60° C. and 120° C.

Step (f) is performed for at most 48 h, preferably for at most 12 h.

Step (f) is performed during a time comprised between 12 h and 96 h, preferably between 12 h and 48 h.

Step (g) is performed by filtration, by centrifugation, by dialysis or by using flocculating agents followed by filtration.

A step of washing the solid obtained in step (g) is carried out before step (h). With preference, said step of washing is carried out 2 times, more preferably 3 times, even more preferably 4 times. Said step of washing can be advantageously carried out with water.

Step (h) is performed under autogenous pressure with a relative humidity of 50 to 80% and/or step (h) is carried out at a temperature ranging from 400° C. to 800° C. under an air, oxygen or inert atmosphere.

In a second embodiment, alternative or complementary to said first embodiment, said catalyst can preferably be prepared according to the following steps:

a1) providing a synthetic zeolite material;

b1) optionally, washing said synthetic zeolite material and drying it at a temperature of at least 50° C. for at least 2 h;

c1) optionally, calcining at a temperature of at least 200° C. for at least 1 h the synthetic zeolite material obtained at step (a1) or step (b1) if said step (b1) is carried out;

d1) putting said synthetic zeolite material in an aqueous solution comprising at least one source of an alkali metal M' and at least one source of metal M, wherein both sources of M and M' are fully soluble in water and wherein the molar ratio M'/M is of at least 1 and the weight ratio of said synthetic zeolite over said aqueous solution is of at most 1000;

e1) optionally, stirring the solution obtained at step (d1) for at least 30 min, preferably at room temperature and/or atmospheric pressure;

f1) heating the solution for at least 12 h and at a temperature of at least 50° C., preferably under autogenous pressure so that the solution does not evaporate;

g1) separating the solid from said liquid obtained at step (f1);

h1) drying the solid obtained at step (g1) and calcining it at a temperature of at least 200° C. for at least 1 h and recovering said catalyst.

In a first alternative, said at least one source of an alkali metal M' and said at least one source of metal M originate from the same compound, with preference said at least one source of an alkali metal M' and said at least one source of metal M is a sodium or a potassium salt of the metal M. More preferably, said at least one source of an alkali metal M' and said at least one source of metal M originate from $Na_2WO_4.2H_2O$, $K_2WO_4$, $NaVO_3$, $KVO_3$, $Na_2MoO_4.2H_2O$, $K_2MoO_4$, $Na_2SnO_3.3H_2O$, $K_2SnO_3.3H_2O$, $Na_2ZrO_3$ or $K_2ZrO_3$.

In a second alternative, said at least one source of an alkali metal M' and said at least one source of metal M originate from two different compounds; with preference said at least one source of metal M is a salt soluble together with said at least one source of an alkali metal M' in water. More preferably, said at least one source of metal M is an ammonium salt, even more preferably $(NH_4)_6Mo_7O_{24}$.

With preference, whatever is the framework type of the synthetic zeolite material and whatever is the alternative chosen among the first alternative and the second alternative, one or more of the following features can be used to better define the preparation of said catalyst as defined in the second embodiment:

Said at least one source of alkali metal M' is selected from Li, Na, K, or Cs.

The washing of step (b1) is carried out with water.

The washing of step (b1) is performed 2 times, preferably 3 times, more preferably 4 times.

The drying of step (b1) is performed at at least 60° C., preferably at at least 75° C. even more preferably at at least 90° C.

The drying of step (b1) is performed for at least 4 h, preferably for at least 8 h, more preferably for at least 24 h, and for at most 72 h, preferably for at most 48 h.

The drying of step (b1) is performed by freeze-drying.

The optional step (c1) is carried out at a temperature ranging from 400° C. to 800° C., preferably from 450 to 750° C., more preferably from 500 to 600° C.

The optional step (c1) is carried out under an air, oxygen or inert atmosphere, preferably at atmospheric pressure.

The optional step (c1) is carried out for at least 8 h, preferably for at least 24 h, more preferably for at least 48 h; and for at most 96 h, preferably at most 72 h.

The molar ratio M'/M in the aqueous solution containing M and M' ranges from 1 to 200, preferably from 2 to 100.

The weight ratio of said synthetic zeolite material over said aqueous solution containing M and M' ranges from 0.01 to 1000, preferably from 0.03 to 25.

Step (f1) is performed at a temperature ranging from 60° C. to 120° C., and/or during at least 24 h, preferably at least 48 h, more preferably at least 72 h, and for at most 96 h.

Step (g1) is performed by filtration, by centrifugation, by dialysis or by using flocculating agents followed by filtration.

A step of washing the solid obtained in step (g1) is carried out before step (h1). With preference, said step of washing is carried out 2 times, more preferably 3 times, even more preferably 4 times. Said step of washing can be advantageously carried out with water.

The drying of the steps (h1) is performed at at least 60° C., preferably at at least 75° C. even more preferably at at least 90° C.

The drying of step (h1) is performed for at least 4 h, preferably for at least 8 h, more preferably for at least 24 h, and for at most 72 h, preferably for at most 48 h.

The drying of step (h1) is performed by freeze-drying.

The calcination of step (h1) is carried out at a temperature ranging from 400° C. to 800° C., preferably from 450 to 750° C., more preferably from 500 to 600° C.

The calcination of step (h1) is carried out under an air, oxygen or inert atmosphere, preferably at atmospheric pressure.

The calcination of step (h1) is carried out for at least 8 h, preferably for at least 24 h, more preferably for at least 48 h; and for at most 96 h, preferably at most 72 h.

Definitions

Zeolite codes (e.g., MWW . . . ) are defined according to the "*Atlas of Zeolite Framework Types*", 6th revised edition, 2007, Elsevier, to which the present application makes reference.

Within the meaning of the present disclosure, the term "clear aqueous suspension", or "water-clear suspension" is understood as it is commonly understood. It means that the suspension appears clear to the eye. In other words, it can be understood as meaning that the aqueous suspension has approximately the same refractive index as water.

Within the meaning of the present disclosure, the term "monodisperse single nanocrystals" is understood to mean that the statistical distribution of the size of the single nanocrystals is relatively narrow.

Within the meaning of the present disclosure, the term "single nanocrystals" is understood to mean individual nanocrystals or non-agglomerated nanocrystals.

Within the meaning of the present disclosure, $TAA_2O$ is the product formed after step (a) and directly derived from the tetraalkylammonium hydroxide structure-directing agent (TAAOH) starting material. $TAA_2O$ is a bis (tetraalkylammonium) oxide compound.

Within the meaning of the present disclosure, the term "silanol-free" is understood to mean zeolite crystals comprising a negligible amount of silanol-defective sites, arising from the presence of silanols and/or silanol nests. Said material is consequently highly hydrophobic due to the absence of Si—OH moistures. Silanol defects are quantified using (i) IR characterization of activated (calcined) samples, or alternatively (ii) using $^{29}$Si-NMR. The presence or absence of defects is determined by the techniques described above. In particular, the relative amount of defects are evaluated following the procedure reported in the studies of Grand J. et al. (*Nature Materials*, 2017, 16, 1010-1015), or of Dubray F. et al. (*J. Am. Chem. Soc.*, 2019, 141, 8689-8693).

Within the meaning of the present disclosure, the term "non-oxidative" means that the concentration of oxidizing agents such as oxygen or nitrogen oxides in the first stream provided at step (i) of the claimed process is below 5% by weight, preferably below 1 wt. %, more preferably below 0.1 wt. %. Most preferably, the mixture is free of oxygen.

Within the meaning of the present disclosure, the term "barg" means "bar gauge". Gauge pressure is zero-referenced against ambient air pressure, so it is equal to absolute pressure minus atmospheric pressure.

Within the meaning of the present disclosure, the term "bara" means "bar absolute". Absolute pressure is zero-referenced against a perfect vacuum, using an absolute scale, so it is equal to gauge pressure plus atmospheric pressure.

TABLE 1

| Sample | Mo-MFI-1 | Mo-MFI-2 | SnMFI | SiMFI |
|---|---|---|---|---|
| Space group | P21/n (monoclinic) | P21/n (monoclinic) | P21/n (monoclinic) | Pnma (orthorhombic) |
| a | 19.8876(6) | 19.9046(6) | 19.8858(0) | 19.8868(6) |
| b | 20.1177(4) | 20.1308(9) | 20.1174(2) | 20.0577(5) |
| c | 13.3858(9) | 13.3900(9) | 13.3835(8) | 13.3701(5) |
| α | 90 | 90 | 90 | 90 |
| β | 90.5491(3) | 90.5985(6) | 90.5296(1) | 90 |
| γ | 90 | 90 | 90 | 90 |
| Volume (Å$^3$) | 5355.37(9) | 5365.09(5) | 5353.88(4) | 5333.13(0) |
| GOF[a] | 1.42 | 1.49 | 1.68 | 1.36 |
| Rp[b] | 2.74 | 2.69 | 3.04 | 3.85 |
| wRp[c] | 3.57 | 3.64 | 4.16 | 5.08 |

[a]Goodness of fit
[b]Expected R-factor
[c]Weight Profile R-factor

Table 1 showing the Le Bail profile refinement results (unit cell parameters, and refinement values) for MoMFI-1, MoMFI-2, SnMFI, and SiMFI examples. Samples used for Le Bail refinement were recorded from 3 to 80° 2θ for 10 h.

Figure 1:
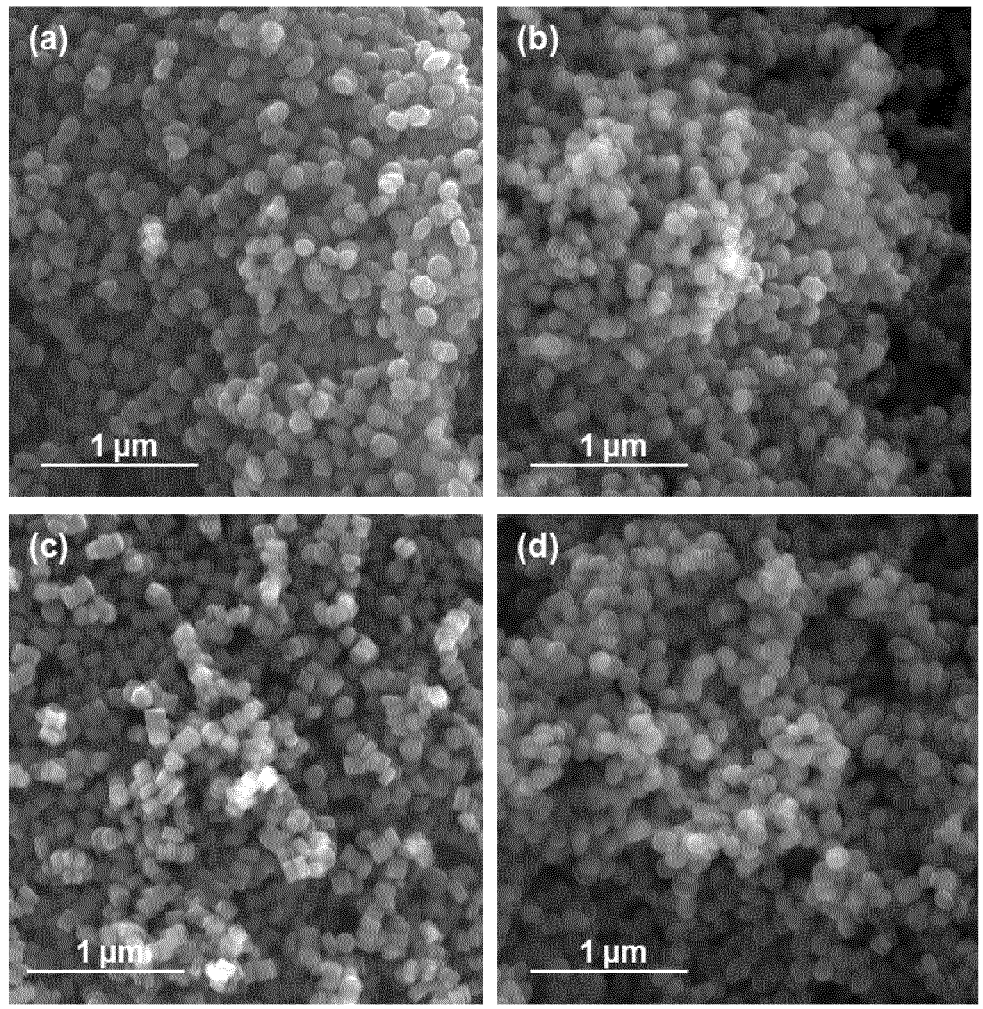
FIG. 1 represents SEM pictures of (a) MoMFI-1, (b) MoMFI-2, (c) SnMFI, and (d) SiMFI samples. The crystal size and morphology correspond to the one from purely siliceous MFI zeolite (silicalite-1) that would be obtained by using the same synthesis procedure without the addition of Molybdenum (FIG. 1*d*). This obtained crystal size (around 150 nm diameter) is approximately twice smaller than the size that would be obtained by using a normal direct synthesis approach from the same gel composition with molybdenum (around 300 nm).
Figure 2:
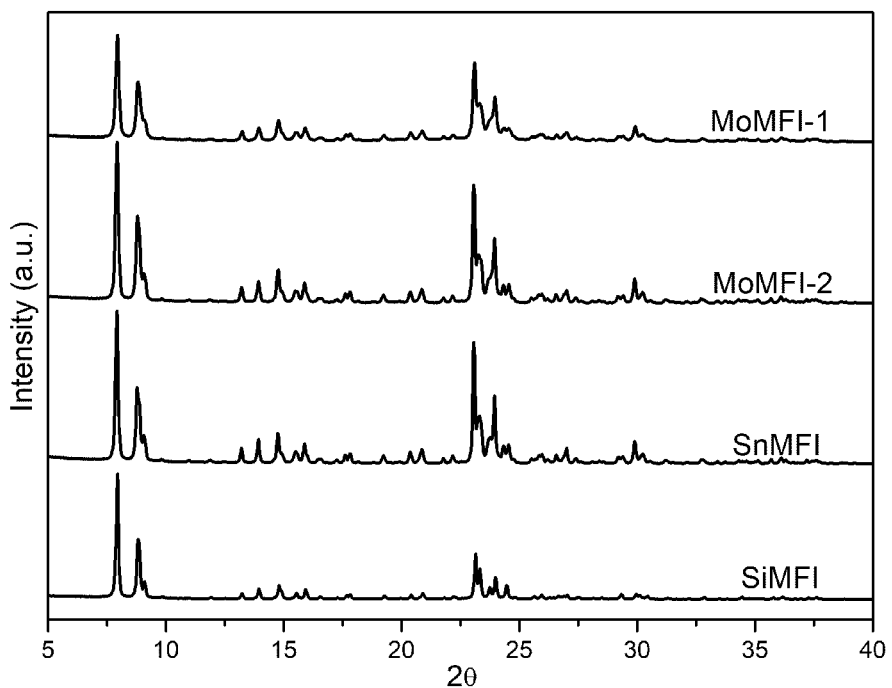
FIG. 2 corresponds to the XRD diffraction patterns of MoMFI-1, MoMFI-2, SnMFI, and SiMFI samples obtained from step h) in the range 3 to 40° 2θ. Only Bragg peaks corresponding to MFI structure are present in all zeolite materials, more specifically, only peaks corresponding to the monoclinic MFI unit cell are observed when it would be expected to have orthorhombic symmetry if only purely siliceous MFI was to be obtained. The monoclinic symmetry can be easily evidenced by the splitting of some diffraction peaks (mainly at 23.30, 23.75, and 24.50° 2θ). Moreover, an expansion of unit cell volume was observed for all samples once compared to purely siliceous silicalite-1 zeolite. Both observations are indicating the presence of heteroatoms (Mo or Sn) in the framework of MFI structure. Details of the Le Bail profile refinement fits are presented in Table 1.
Figure 3:
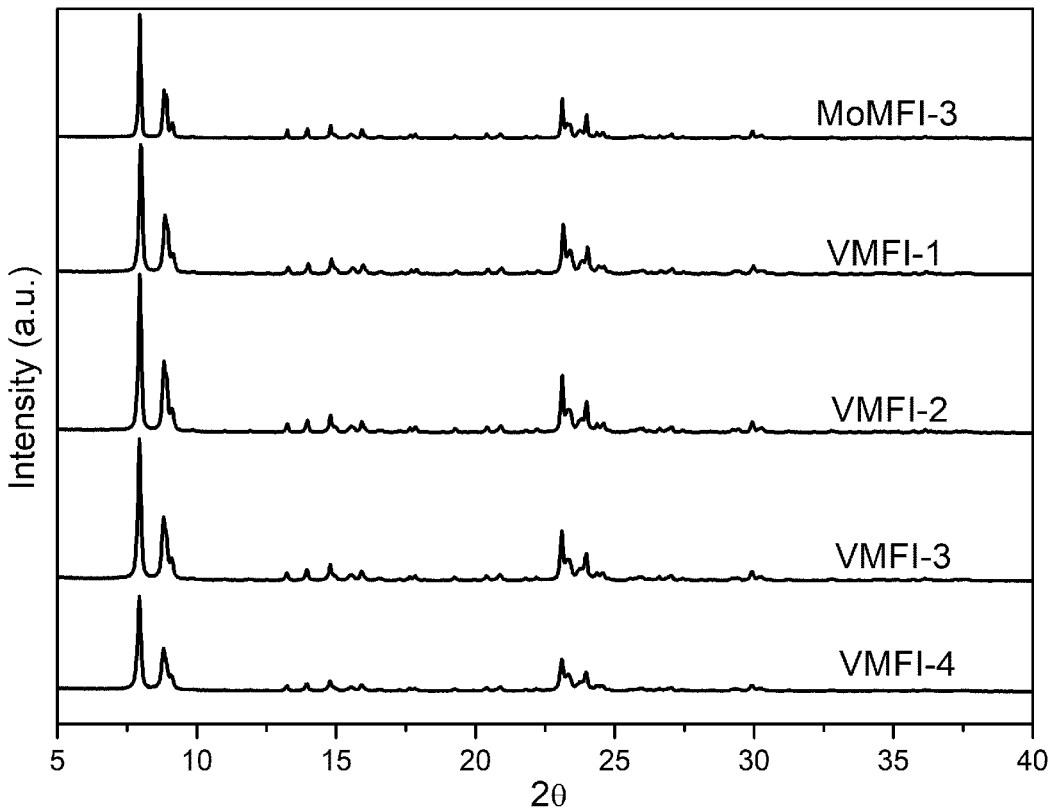

FIG. 3 showing the X-ray diffraction patterns of the samples MoMFI-3, VMFI-1, VMFI-2, VMFI-3, and VMFI-4. All samples exhibit splitting of diffraction peaks (mainly at 23.30, 23.75, and 24.50° 2θ) linked to a monoclinic symmetry, indicative of an effective metal introduction, and healing of silanol defects.

Figure 4:
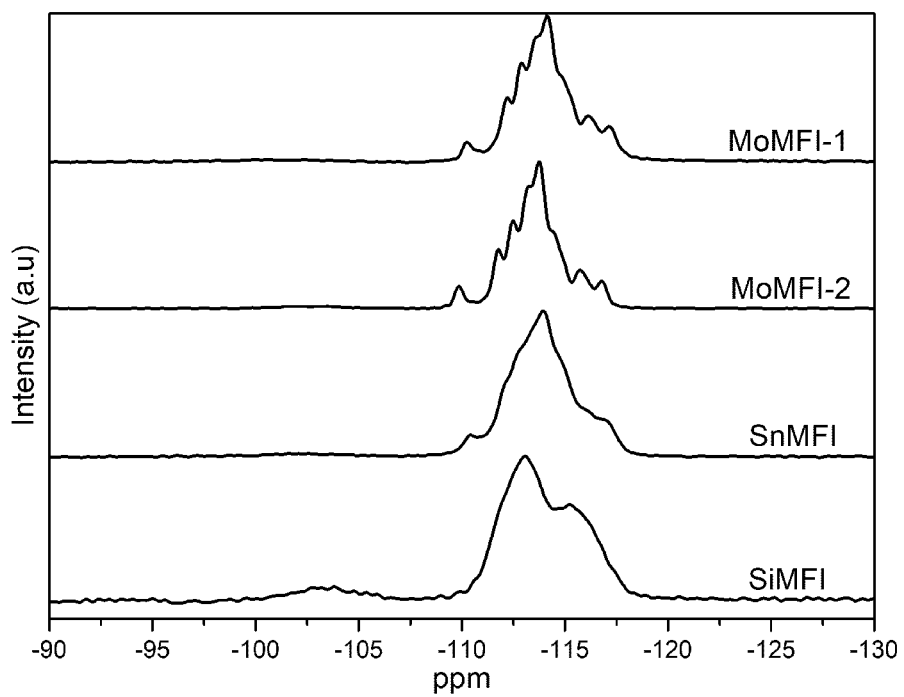

FIG. 4 shows $^{29}$Si solid-state Magic Angle Spining Nuclear Magnetic Resonance (MAS NMR) spectra of MoMFI-1, MoMFI-2, SnMFI, and SiMFI samples obtained after step (h). Absence of Q3 species and high resolution of Q4 species was obtained indicating the very low amount of silanol defects in the metal-containing samples, and the local homogeneity of the samples, with regards to purely siliceous MFI zeolite (sample SiMFI).

Figure 5:
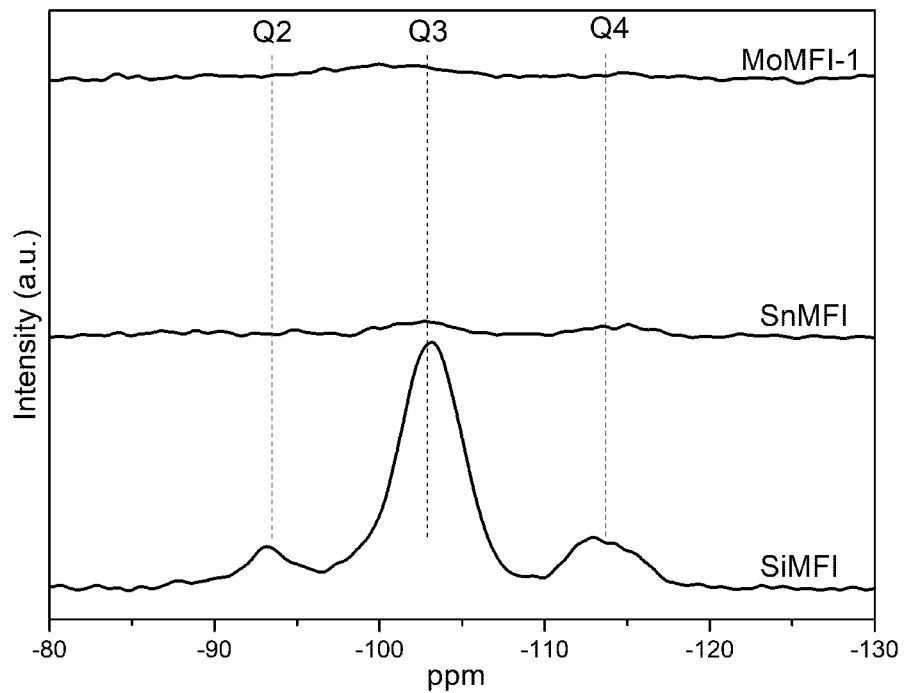

FIG. 5 represents the {$^1$H} $^{29}$Si solid-state Cross Polarization Magic Angle Spining Nuclear Magnetic Resonance (CP MAS NMR) experiment for sample MoMFI-1, SnMFI, and SiMFI, where the absence/negligible amount of silanols is demonstrated through the absence of any signal for both metal-containing samples with regards to sample SiMFI.

Figure 6:
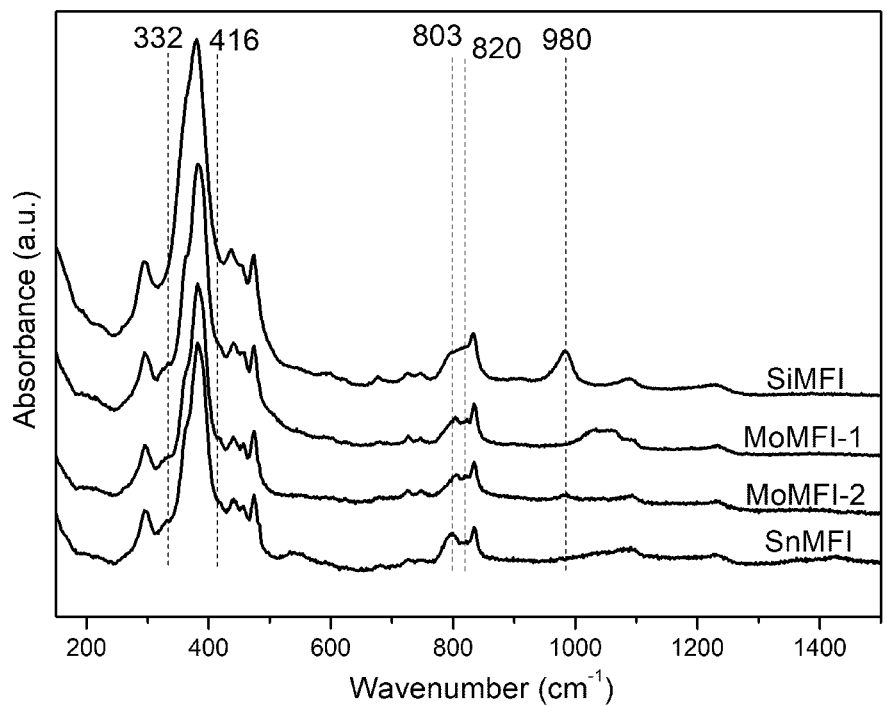

FIG. 6 represents the Raman spectra of samples SiMFI, MoMFI-1, MoMFI-2 and SnMFI. The absence of any metal oxide phase is confirmed for all samples. New contributions at 332, 416, 803, and 820 cm$^{-1}$ indicate the presence of framework metal species. The low amount of silanol defects can also be observed by the absence of a signal at about 980 cm$^{-1}$ for metal-containing zeolites. No peaks corresponding to oxide phase of molybdenum (higher intensity band expected at 980 cm$^{-1}$) or tin (higher intensity band expected at 632 cm$^{-1}$) can be observed, indicating the absence of oxide species in both samples.

Figure 7:
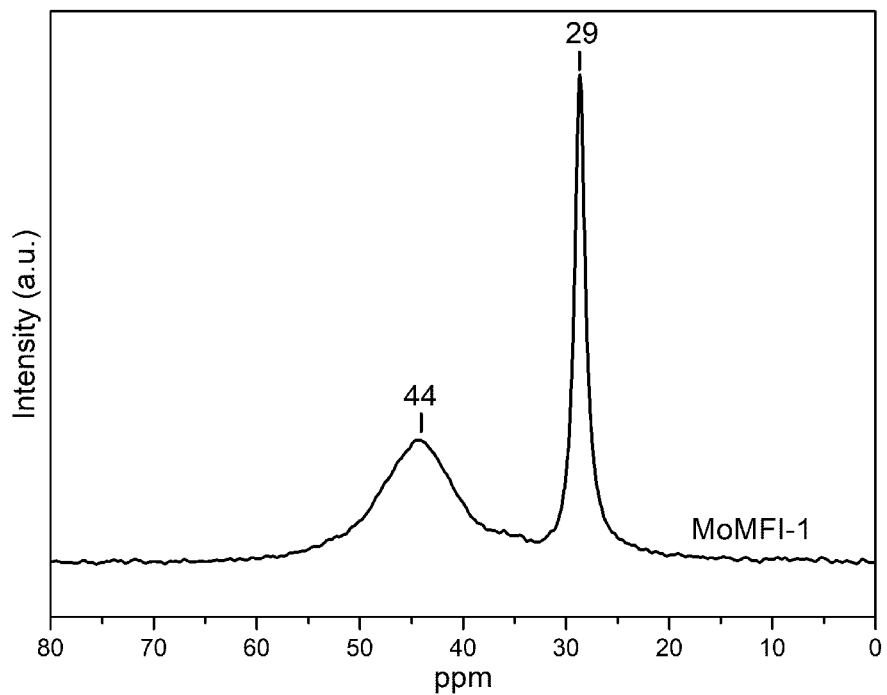

FIG. 7 presents the $^{31}$P solid-state MAS NMR spectra of TMPO interacting with MoMFI-1 sample. Two peaks can be observed at 29 and 44 ppm, corresponding to respectively: physisorbed TMPO and TMPO interacting with Lewis acid sites from the MFI zeolite, which are actual Mo framework sites.

Figure 8:
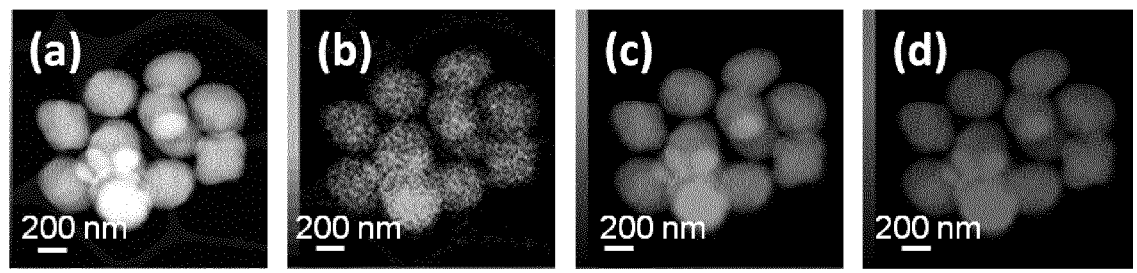

FIG. 8 presents the Scanning Transmission Electron Microscope-Energy Dispersive X-Ray Spectroscopy (STEM-EDS) micrographs (a) of sample MoMFI-1. The homogeneous distribution (b) of Mo, (c) of Si and (d) of O in the MFI framework are shown.

Figure 9:
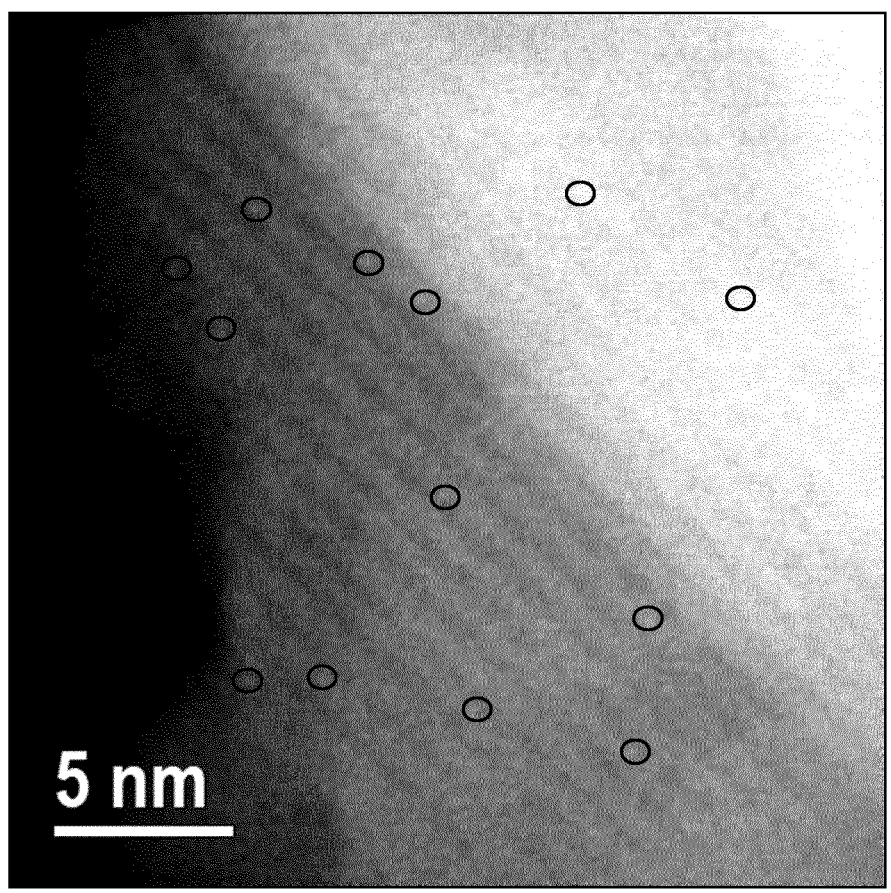

FIG. 9 shows a high-resolution High-Angle Annular Dark Field-Scanning Transmission Electron Microscope (HAADF-STEM) image of sample MoMFI-1. The Z-sensitive contrast obtained using this imaging technique allows observing the presence of the Mo metal sites in the structure. Mo appears as white dots, some of them being highlighted with red circles in the figure. Due to the location and size of these sites, it can be concluded that Mo atoms are atomically dispersed in the zeolite MFI framework.

Figure 10:
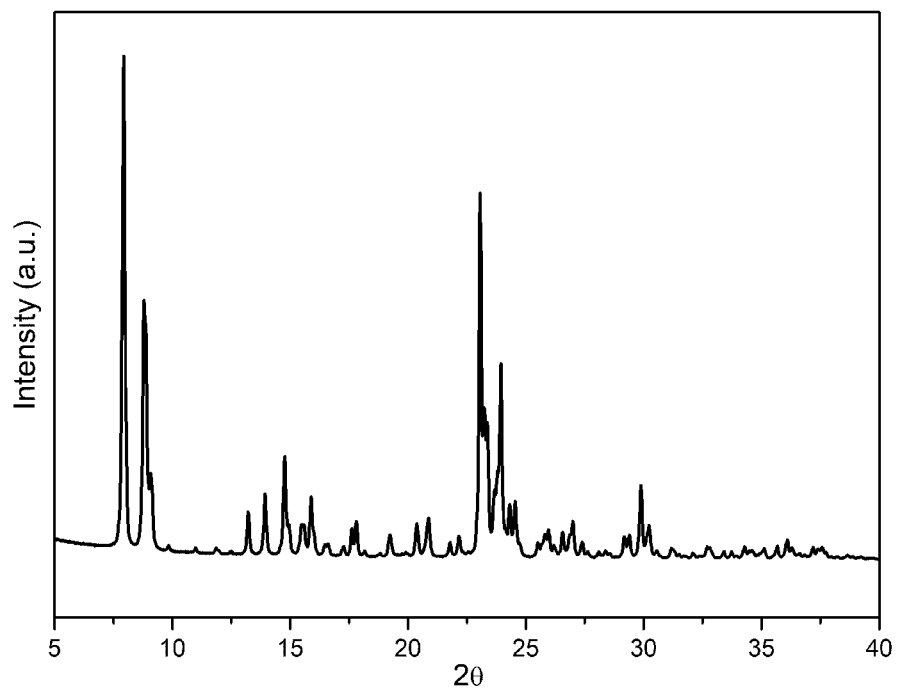

FIG. 10 is an XRD pattern of the sample MoMFI-4.

Figure 11:
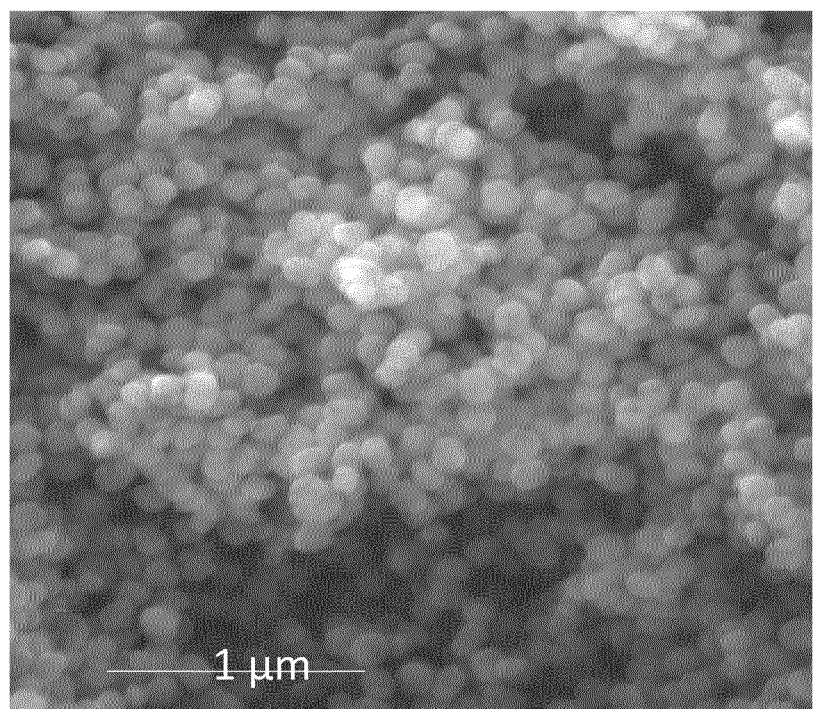

FIG. 11 is an SEM picture of the sample MoMFI-4.

Figure 12:
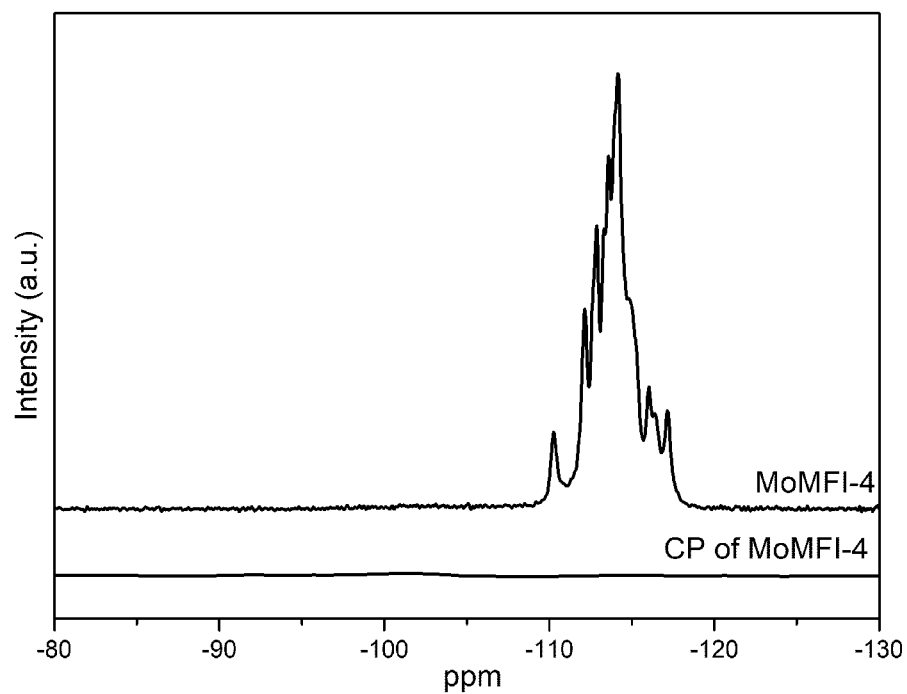

FIG. 12 is a $^{29}$Si MAS NMR and $^{29}$Si CP MAS NMR spectra of sample MoMFI-4.

Figure 13:
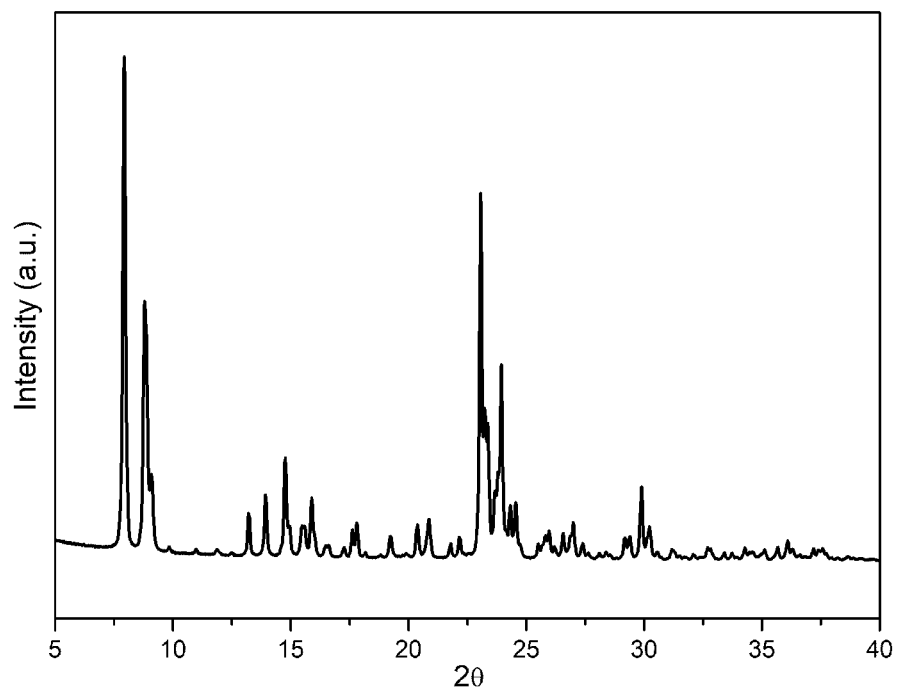

FIG. 13 represents the XRD pattern of sample Mo-Silicalite-1 obtained from step h). Splitting of diffraction peaks at 23.30, 23.75, and 24.50° 2θ is observed and indicates a monoclinic symmetry of the MFI structure instead of the orthorhombic cell.

TABLE 2

| Sample | Mo-Silicalite-1 |
|---|---|
| Symmetry | P21/n (monoclinic) |
| a | 19.9243(5) |
| b | 20.1433(8) |
| c | 13.3985(2) |
| β | 90.6087(3) |
| Volume (Å$^3$) | 5377.10(7) |
| GOF[a] | 1.70 |
| Rp[b] | 2.47 |
| wRp[c] | 3.42 |

[a]Goodness of fit
[b]Expected R-factor
[c]Weight Profile R-factor

Additionally, using Le Bail profile refinement of the diffraction pattern (Table 1), the space group transition towards monoclinic symmetry was confirmed, alongside a unit cell volume expansion at 5377.1 Å$^3$ (to be compared with a volume of average 5330.0 Å$^3$ for purely siliceous MFI (Silicalite-1) zeolite). Both observations indicate the successful introduction of Mo atoms in the Silicalite-1 structure.

Figure 14:
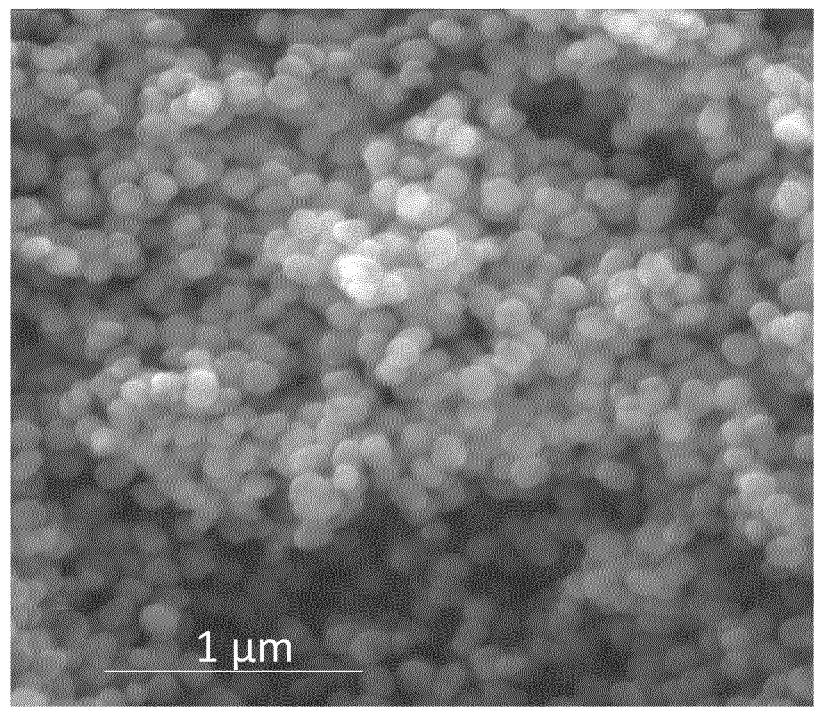

FIG. 14 shows the SEM picture of sample Mo-Silicalite-1 obtained from step (h). Particles of approximately 100 to 150 nm are obtained.

Figure 15:
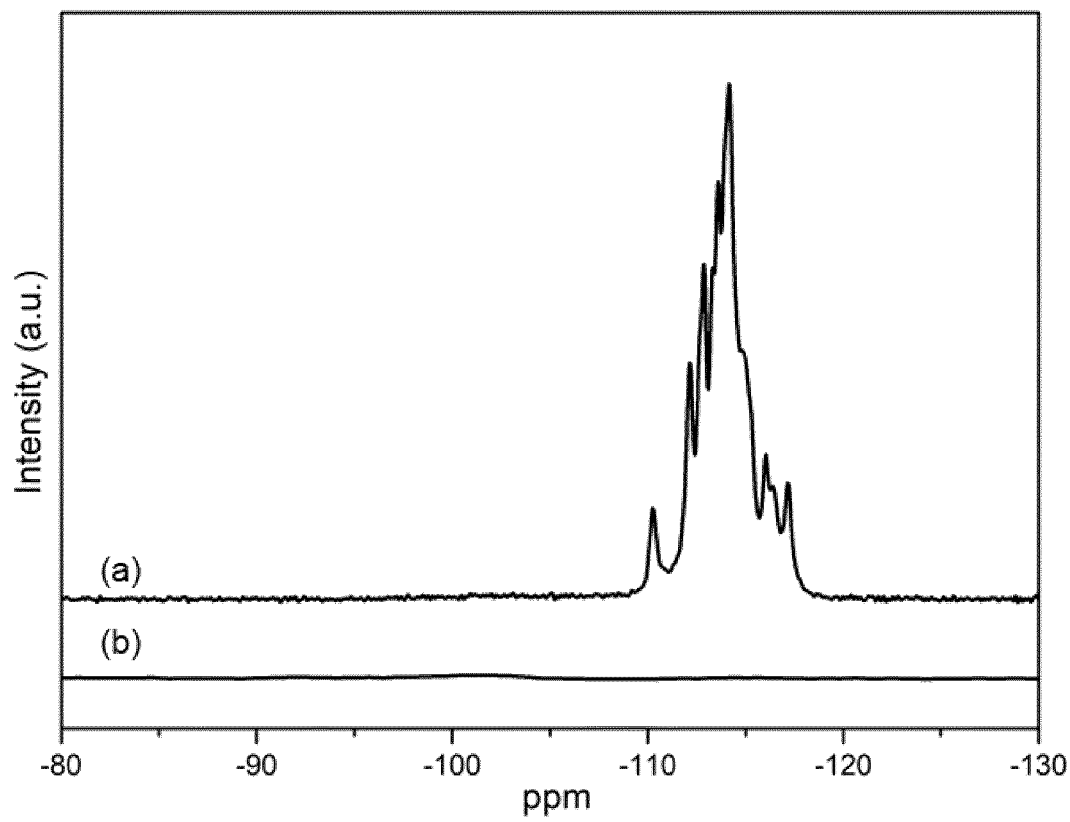

FIG. 15 represents the $^{29}$Si MAS NMR spectrum of sample Mo-Silicalite-1 obtained from step (h), as well as the {$^1$H} $^{29}$Si CP MAS NMR experiment.

No signal is observed on the cross-polarization experiment, indicative of the absence of any silanol species for this sample. This is further supported by the absence of Q3 species in the $^{29}$Si MAS NMR spectrum. Additionally, very high resolution of the Q4 species is achieved, indicative of the very high local homogeneity of the sample, and of the absence of silanol defects.

Figure 16:
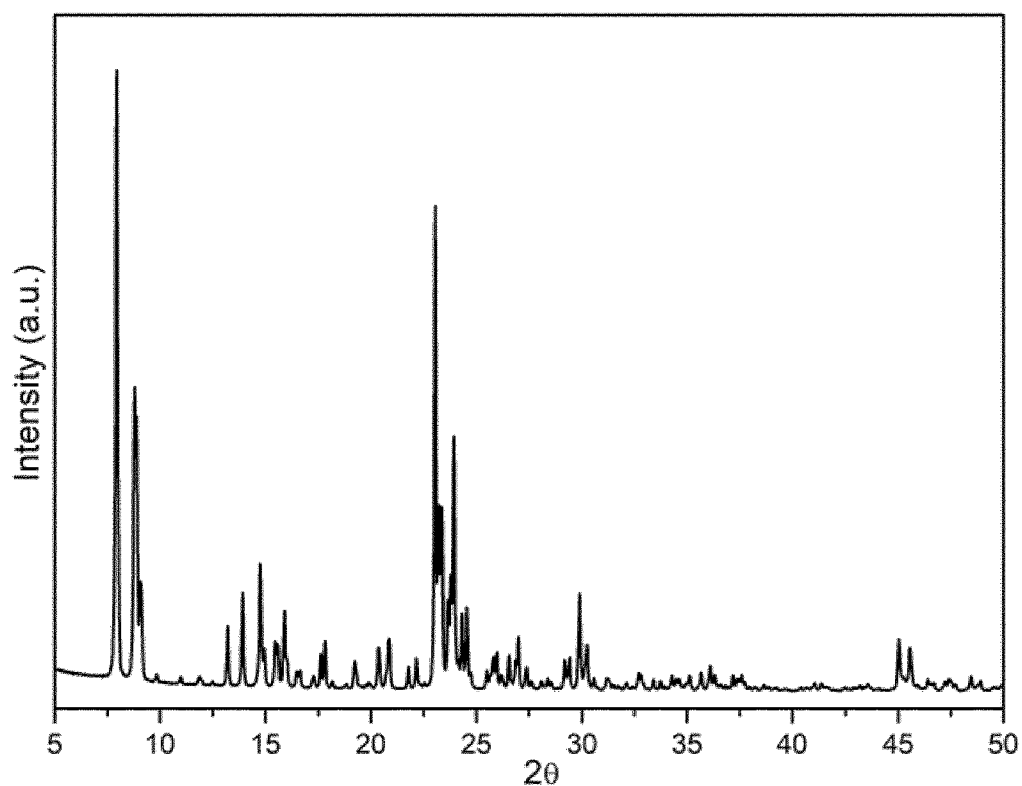

FIG. 16 represents the XRD pattern of sample Mo-ZSM-5 obtained from step (h); Splitting of diffraction peaks at 23.30, 23.75, and 24.50° 2θ is observed indicating the transformation from orthorhombic to monoclinic symmetry of the sample.

TABLE 3

| Sample | Mo-ZSM-5 |
| --- | --- |
| Symmetry | P21/n (monoclinic) |
| a | 19.9101(1) |
| b | 20.1388(3) |
| c | 13.3915(7) |
| β | 90.6088(3) |
| Volume (Å$^3$) | 5369.26(6) |
| GOF$^a$ | 1.60 |
| Rp$^b$ | 2.89 |
| wRp$^c$ | 3.97 |

$^a$Goodness of fit
$^b$Expected R-factor
$^c$Weight Profile R-factor

In addition, using Le Bail profile refinement of the following XRD pattern (Table 2), the space group transition towards monoclinic symmetry is confirmed, and expansion of the unit cell volume with regards to the initial material from 5353.81 to 5369.27 Å$^3$ is measured. The higher unit cell volume of the initial ZSM-5 sample used in the preparation of Mo-ZSM-5 is attributed to the presence of molybdenum in the framework.

Figure 17:
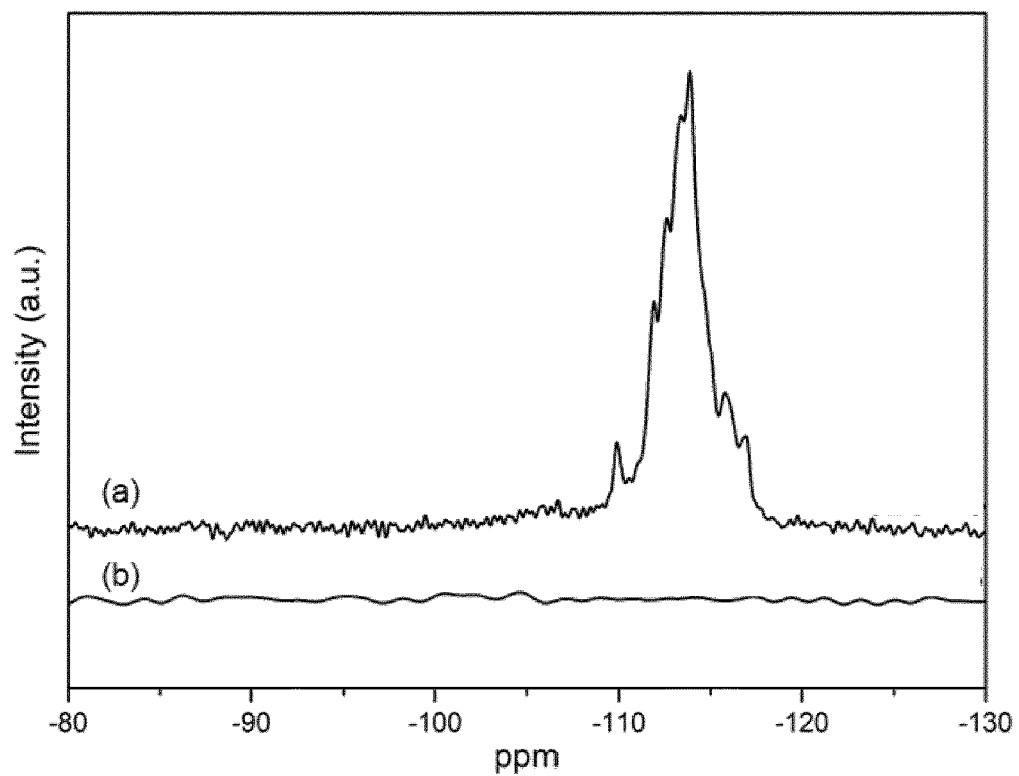

FIG. 17 represents the $^{29}$Si MAS NMR spectrum of sample Mo-ZSM-5 obtained from step (h), as well as the $\{^1H\}$ $^{29}$Si CP MAS NMR spectrum.

The absence of any silanol species for this sample is confirmed: no peaks corresponding to Q2 and Q3 are present in the $\{^1H\}$ $^{29}$Si CP MAS NMR spectrum (FIG. 5). Additionally, the Q4 species are present with high resolution indicating the high local homogeneity of the sample, and the absence of silanol defects, as they are cured by the addition of Mo.

Figure 18:
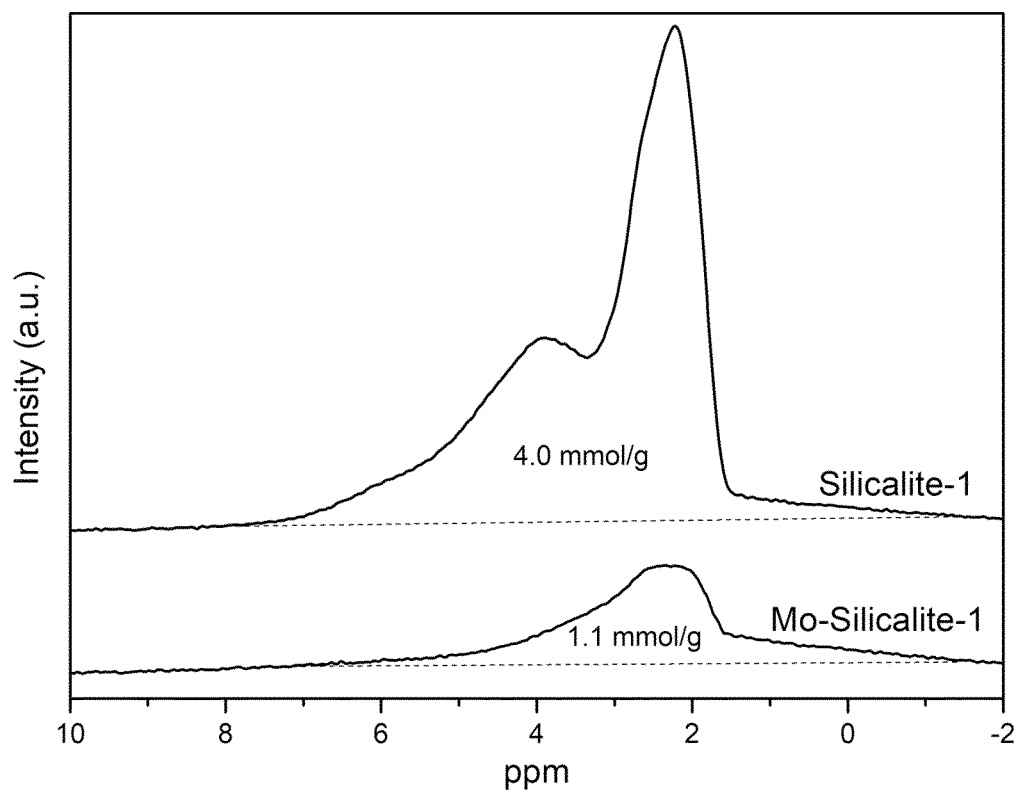
Figure 18:
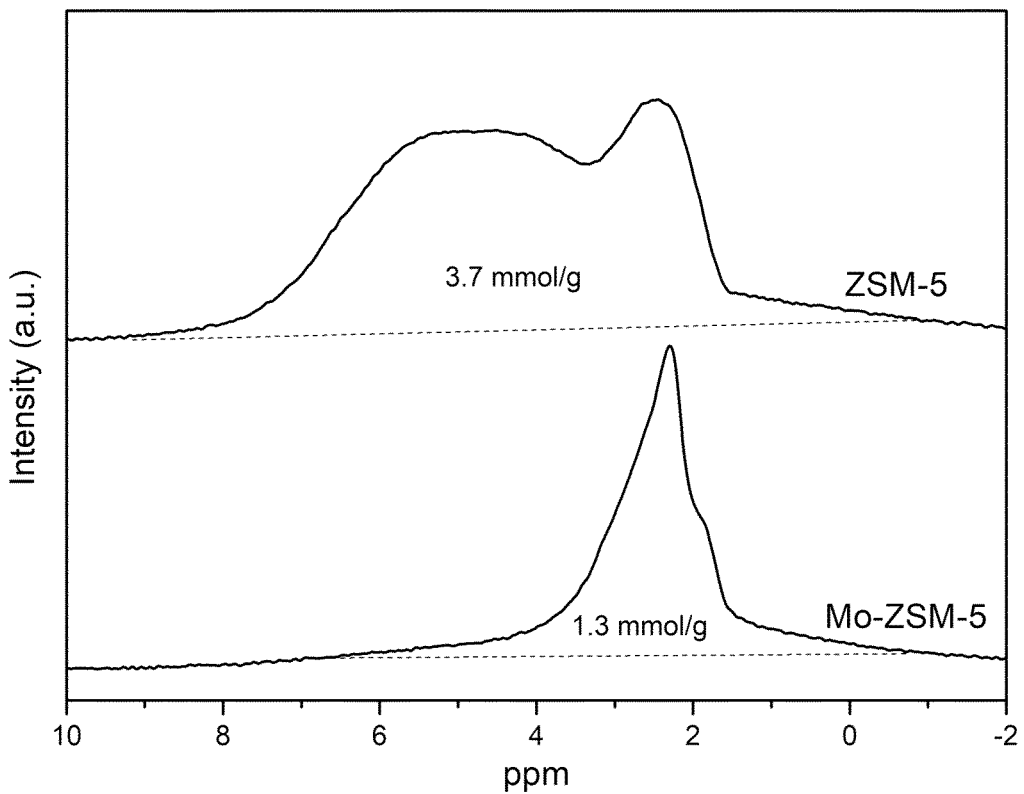

FIG. 18 represents $^1$H MAS NMR of dehydrated zeolite samples silicalite-1, Mo-silicaliste-1, ZSM-5 and Mo-ZSM-5.

Figure 19:
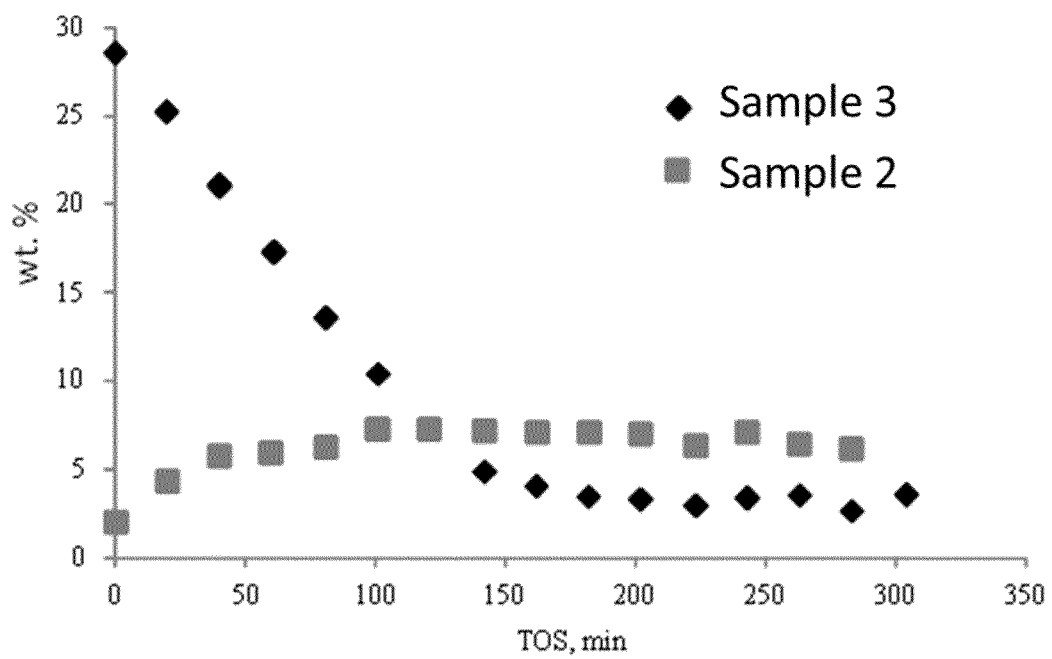

FIG. 19. Methane conversion a function of time on stream for Sample 2 and Sample 3 obtained catalysts. Conditions: 1123K, atmospheric pressure, 0.3 g of catalyst, WHSV 1.22 h$^{-1}$.

Figure 20:
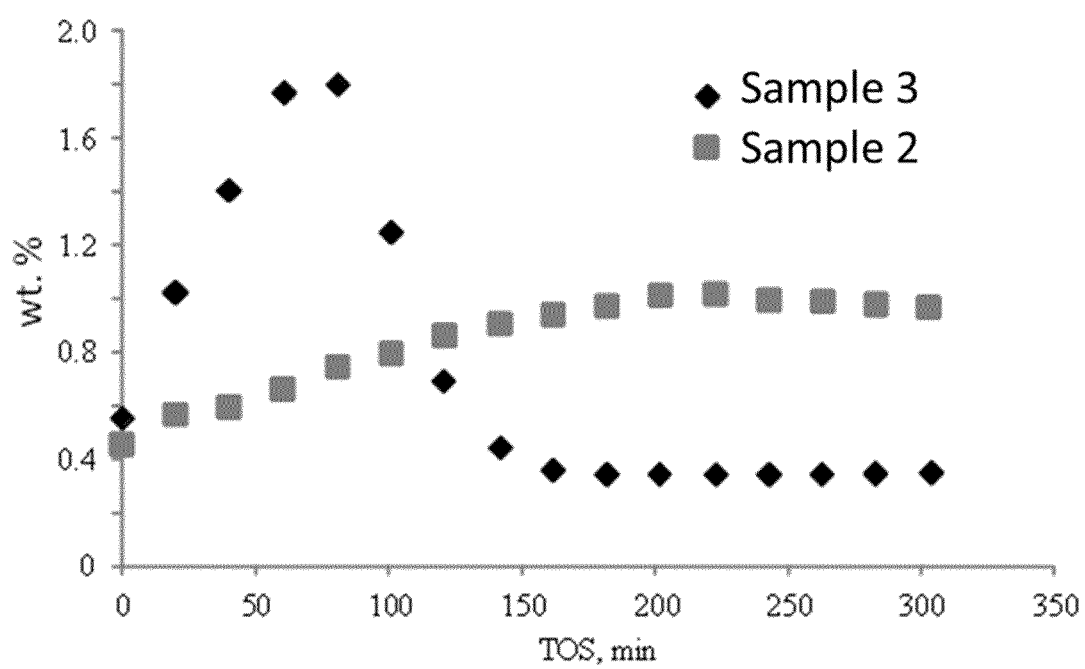

FIG. 20. C2 hydrocarbons yield as a function of time on stream for Sample 2 and Sample 3 catalysts. Conditions: 1123K, atmospheric pressure, 0.3 g of catalyst, WHSV 1.22 h$^{-1}$.

DETAILED DESCRIPTION

With regards to the process for the conversion of methane into ethylene, this reaction is depicted below:

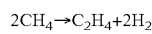

$2CH_4 \rightarrow C_2H_4 + 2H_2$

The conversion of methane into ethylene, under non-oxidative conditions, is typically carried out in a reactor comprising a catalyst, which is active in the conversion of the methane-containing gas stream to ethylene. The methane-containing gas stream that is fed to the reactor comprises more than 50% vol. methane based on the total volume of said methane-containing gas stream, preferably more than 70% vol. methane and more preferably of from 75% vol. to 100% vol. methane. The balance of the methane-containing gas may be other alkanes, for example, ethane, propane and butane. The methane-containing gas stream may be natural gas which is a naturally occurring hydrocarbon gas mixture consisting primarily of methane, with up to about 30 vol. % concentration of other hydrocarbons (usually mainly ethane and propane), as well as small amounts of other impurities such as carbon dioxide, nitrogen and others. The conversion of a methane-containing gas stream is carried out at a weight hourly space velocity of from 0.1 to 100 h$^{-1}$, a pressure of from 0.5 to 50 bar and a temperature of from 800 to 1100° C. More preferably, the conversion is carried out at WHSV of from 0.5 to 50 h$^{-1}$, a pressure of from 0.5 to 10 bar and a temperature of from 820 to 1000° C. Even more preferably, the conversion is carried out at WHSV of from 1 to 30 h$^{-1}$, a pressure of from 0.5 to 8 bar and a temperature of from 840 to 950° C. Various co-feeds such as $CO_2$, steam or hydrogen or mixtures thereof that react with coke precursors or prevent their formation during methane aromatization can be added at levels of <30% vol. to the methane-containing feed to improve the performance of the catalyst.

The first stream of the process of the disclosure may originate from hydrocarbon or mixtures of hydrocarbons comprising natural gas (e.g., CH$_4$), associated petroleum gas, liquefied petroleum gas comprising C2-C5 hydrocarbons, C6+ heavy hydrocarbons (e.g., C6 to C24 hydrocarbons such as diesel fuel, jet fuel, gasoline, tars, kerosene, etc.), and the like, or combinations thereof. In an embodiment, the reactant mixture can comprise natural gas. Generally, natural gas is composed primarily of methane, but can also contain ethane, propane and heavier hydrocarbons (e.g., iso-butane, n-butane, iso-pentane, n-pentane, etc.), as well as very small quantities of nitrogen, oxygen, carbon dioxide, sulfur compounds, and/or water. In some embodiments, the natural gas can be provided from a variety of sources including, but not limited to, gas fields, oil fields, coal fields, fracking of shale fields, biomass, biogas, landfill gas, and the like, or combinations thereof.

In an embodiment, the first stream can include a stream from a refinery and/or processing plant. For example, light alkanes, including methane, can often be separated in a refinery during the processing of crude oil into various products, and a methane feed stream can be provided from the same refinery, a different refinery, and/or a refinery off-gas. The methane feed stream can include a stream from combinations of different sources (e.g., streams from different refineries, different streams from the same refinery, etc.). The methane feed stream can be provided from a remote location and initial processing of the stream (e.g., refining or partial refining) can occur at the remote location to remove certain contaminants; the refining or partial refining can occur on-site where the non-oxidative coupling of CH$_4$ reaction is conducted, or both.

In an embodiment, the first stream does not contain sulfur-containing compounds (e.g., SOx, such as SO$_2$, S, and/or RSyR' type compounds). The first stream can be substantially free of sulfur-containing compounds, or alternatively essentially free of sulfur-containing compounds. In an embodiment, the reactant mixture can comprise sulfur-containing compounds in an amount of less than about 1 mol %, preferably less than about 0.5 mol %, preferably less than about 0.1 mol %; more preferably, less than about 0.01 mol %, even more preferably less than about 0.001 mol %, and most preferably less than about 0.0001 mol %. In embodiments, sulfur-containing compounds can be removed from the first stream before the reaction at step (iii).

In another embodiment, the first stream can comprise at least 50 ppm of sulfur (S) and/or sulfur-containing compounds (e.g., SOx, such as SO$_2$, and/or RSyR' type compounds). Without wishing to be limited by theory, S and/or sulfur-containing compounds can reduce and/or prevent coke formation in a reactor, in a manner similar to reducing and/or preventing coke formation in thermal cracking furnaces such as ethane steam crackers. SOx, compounds can be reduced to $H_2S$ under a reducing environment. Further, without wishing to be limited by theory, while S and/or sulfur-containing compounds could become incorporated into a reaction product and lower selectivity to desired products as well as to deactivate certain catalysts, in a reducing environment with plenty of $H_2$ and high temperatures, S and/or sulfur-containing compounds could be converted into $H_2S$, which could help "immunize" the reactor walls by inhibiting coke formation.

In other embodiments, the first stream can exclude S and/or sulfur-containing compounds. In an embodiment, the first stream can be substantially free of S and/or sulfur-containing compounds, or alternatively essentially free of S and/or sulfur-containing compounds. In an embodiment, the first stream can comprise S and/or sulfur-containing compounds in an amount of less than about 1 mol %, preferably less than about 0.5 mol %, preferably less than about 0.1 mol %, preferably less than about 0.01 mol %, preferably less than about 0.001 mol %, or preferably less than about 0.0001 mol %. In some embodiments, S and/or sulfur-containing compounds can be removed from the reactant mixture before introducing the first stream to the reactor.

In an embodiment, the first stream can further comprise a diluent. In some embodiments, the diluent can be inert for the non-oxidative coupling of $CH_4$ reaction (e.g., "inert diluent"), e.g., the diluent does not participate in the non-oxidative coupling of $CH_4$ reaction. In other embodiments, the diluent can be a reactant or a product of a non-oxidative coupling of $CH_4$ reaction, such as hydrogen ($H_2$). In an aspect, an inert diluent can be introduced to the reactor in a staged addition fashion. In embodiments where the diluent is a reactant or a product of a non-oxidative coupling of $CH_4$ reaction, the diluent can also be referred to as an "active diluent" or an "active co-feed," as the diluent can be "active" for shifting the equilibrium of the non-oxidative coupling of $CH_4$ reaction, interacting with a catalyst, etc. As will be appreciated by one of skill in the art, and with the help of this disclosure, the addition to the reactor or any zone thereof of either a product or additional reactant will shift the reaction equilibrium, changing the extent of reaction, the conversion, and the final product mix.

In some configurations, a diluent can be added to the first stream before entering the reactor (e.g., before entering the preheat zone of the reactor). Additionally or alternatively, a diluent containing stream can be introduced to the reactor independently of the first stream comprising the reactant mixture. Non-limiting examples of inert diluents suitable for use in the present disclosure can include nitrogen, inert gases, argon, neon, helium, krypton, xenon, carbon monoxide, carbon dioxide, and the like, or combinations thereof. Without wishing to be limited by theory, while carbon monoxide and carbon dioxide can be produced during non-oxidative coupling reactions, they are not expected to influence the equilibrium of the non-oxidative coupling reactions to a significant extent, e.g., they are not expected to influence the equilibrium of the non-oxidative coupling reactions to the same extent that hydrogen does, for example; and as such can be considered "inert" diluents. Non-limiting examples of active diluents suitable for use in the present disclosure can include hydrogen, steam, natural gas components other than methane, ethane, propane, butanes, unsaturated hydrocarbons, and the like, or combinations thereof.

In an embodiment, the diluent (e.g., inert diluent and/or active diluent) can be present in the first stream in an amount of from about 0.01% to about 95%, alternatively from about 0.1% to about 20%, or alternatively from about 1% to about 10%, based on the total volume of the reactant mixture.

In some embodiments, an $H_2$-containing stream can be added to the first stream before entering the reactor (e.g., before entering the preheat zone of the reactor), to enrich the reactor environment with $H_2$. Additionally or alternatively, an $H_2$-containing stream can be added at step (iii) to enrich the environment of the reactor or a zone thereof with $H_2$, for example via an $H_2$-containing stream-fed directly to the reactor or a zone thereof independently of the feed stream comprising the reactant mixture. Without wishing to be limited by theory, the addition of hydrogen, a product of the non-oxidative coupling reaction, to the reactor or a zone thereof controls the reaction equilibria in both the gas phase (e.g., $H_2$ impacts gas-phase reactions) and on the catalytic surface (e.g., $H_2$ impacts surface catalysis reactions), when a catalyst is used in the process. Further, without wishing to be limited by theory, the addition of hydrogen can decrease the production of larger hydrocarbons, such as aromatic hydrocarbons, via hydrogenation and hydrocracking reactions, and consequently, the formation of coke can be decreased. Hydrogen can help control the conversion and selectivity. As will be appreciated by one of skill in the art, and with the help of this disclosure, hydrogen can decrease methane conversion. In an embodiment, the addition of hydrogen to the reactor can increase the selectivity to ethylene, when compared to an otherwise similar process that employs the non-oxidative coupling of $CH_4$ reaction without hydrogen addition to the reactor. Further, as will be appreciated by one of skill in the art, and with the help of this disclosure, the amount of hydrogen that is introduced to the reactor has to be optimized for each particular reactor system to minimize the decrease in methane conversion and to maximize the increase in selectivity to ethylene.

In an embodiment, the catalyst is pre-treated before the reaction with a stream containing CO, $CO_2$, $C_2H_4$, $C_2H_6$, $H_2O$, $C_3$+ hydrocarbon mixture containing at least 10 wt. % of acyclic hydrocarbons or a mixture of thereof,
 at a temperature between 450° C. and 850° C., for example between 450° C. and 750° C.; and/or
 WHSV between 0.1 and 100 h-, and/or
 a pressure between 0.1 and 10 barg.

In an embodiment, the pre-treatment will be performed with $CH_4$-containing stream at WHSV between 0.1-1.5 h$^{-1}$, temperature range 650° C.-850° C. and pressure 1-10 barg.

In an embodiment, the reactor used at step (iii) can comprise a tubular reactor, a continuous flow reactor, a riser reactor, a reformer reactor, a fixed bed reactor, a shock tube reactor, a multi-tubular reactor, a membrane reactor, a dual flow reactor, a gauze reactor, a fluidized bed reactor, a moving bed reactor, a continuous stirred-tank reactor (CSTR), a plug flow reactor (PFR), a microchannel reactor, a modular reactor, a modular microchannel reactor, a honeycombed monolithic reactor, a honeycombed wall filter monolithic reactor, and the like, or combinations thereof. In an embodiment, the reactor can comprise a reformer reactor, a fixed bed reactor, a fluidized bed reactor, a moving bed reactor, and the like, or combinations thereof.

The disclosure relates to a method for the preparation of a synthetic zeolite material, containing at least one metal M with silicon to metal M molar ratio Si/M ranging from 100 to 65440 as determined by inductively coupled plasma optical emission spectrometry, wherein said method comprises the following steps:

a) contacting at least one source of silicon, at least one tetraalkylammonium hydroxide structure-directing agent (TAAOH) and water, to obtain an aqueous suspension having the following molar composition (I):

$$1SiO_2:yTAA_2O:zH_2O$$

in which:
0.04<y<0.40, preferably 0.2<y<0.3,
8<z<120, preferably 20<z<50.

b) ageing during a time ranging between 1 h and 100 h the resulting clear suspension from step (a) at a temperature ranging from 10° C. to 50° C., preferably 10 to 35° C.;

c) heating for at least 30 min the clear suspension of step (b) at a temperature ranging from 40° C. to 180° C., preferably at a temperature ranging from 60° C. to 120° C.;

d) cooling the solution obtained at step (c) to 20° C. and adding at least one source of alkali metal M' selected from Li, Na, K, or Cs and at least one metal M, to obtain a gel having the molar composition (II):

$$xM_nO_m:1SiO_2:yTAA_2O:wM'_2O:zH_2O$$

In which: the M'/M ratio varies from 0.1 to 4
0.04<y<0.40, preferably 0.2<y<0.3,
8<z<120, preferably 20<z<50,
0.0004<x<0.15, preferably 0.01<x<0.1,
0.0004<w<0.30, preferably 0.01<w<0.2,
n is an integer equal to 1 or 2, and
m is an integer and 1<m<6;

e) ageing said gel obtained at step (d) at a temperature ranging from 10° C. to 35° C. for at least 30 min;

f) heating the solution obtained at step (e) at a temperature ranging from 40° C. to 180° C., for at least 12 h and at most 96 h;

g) separating the solid from said liquid obtained at step (f);

h) calcining said solid obtained at step (g) under autogenous pressure with a relative humidity of 50 to 80% to obtain said synthetic zeolite material.

According to an embodiment of the disclosure, the synthetic zeolite material has an MFI, BEA, MWW or FAU framework type.

According to an alternative embodiment of the disclosure, the synthetic zeolite material has a MOR, EUO, TON, MTT, CHA or MEL framework type.

With regards to the step (a), it consists in the nucleation or at least partial crystallisation of the zeolite material. The precise control of nucleation and crystallization steps can, for instance, be controlled by varying the saturation of the synthetic mixture, by changing water or TAA$_2$O content, by introducing several different TAA$_2$O organic molecules, or by changing the temperature at which are conducted the hydrothermal treatments [in steps (b) and (f)], allowing precise control of particle size and morphology of the synthetic zeolite material. The method according to the present disclosure is particularly advantaging and versatile in that there is no need to have a complete crystallisation at step (a).

Advantageously the water used in step (a) is de-ionized or double-distilled (dd H$_2$O). As an example, double distillation can be performed as follows:

Tape-water is boiled, and the vapours are condensed in a clean container. The retrieved vapours are then boiled again, and retrieved in a second clean container. The as-obtained dd H$_2$O can then be used.

The source of silicon can be selected from any source of silicon able to provide monomeric Si2-Si6 oxihydroxide species, during step (a). Thus, the amount of larger polymerized silica species such as [SiOOH]$_n$ are excluded from the precursor suspensions resulting in the formation of zeolite nanoparticles under hydrothermal treatments [R. M. Barrer, "Hydrothermal Chemistry of Zeolites", 1982, Academic Press, London].

The tetraalkyl orthosilicates are preferred, and tetraethyl orthosilicates are the most preferred. The source of silicon can preferable by selected from silica hydrogel, salicilic acid, colloidal silica, fumed silica, tetraalkyl orthosilicates, silica hydroxides, precipitated silica and sodium silicates.

The tetraalymmonium hydroxide structure-directing agent is preferably tetraethylammonium hydroxide (TEAOH), tetrapropylammonium hydroxide (TPAOH), or tetrabutylammonium hydroxide (TBAOH).

Preferably step (a) does not involve the presence of any other metal atoms than Si i.e. the alkali metals, or metals, including aluminium are not present in step (a).

The water-clear suspension obtained from the molar composition (1) has preferably a pH of about 12 to 14.

In embodiments of the method of preparation, the following sub-steps are performed:

a-a) A solution comprising at TAA$_2$O and double-distilled or de-ionized water is prepared. The solution is then homogenized using preferably a magnetic stirrer.

a-b) To the said solution of step a-a), is then added dropwise the silicon source under vigorous stirring, performed preferably using a magnetic stirrer.

In an embodiment, the suspension obtained after step (a) is placed in a sealed container, to prevent any change of the molar composition that could occur because of evaporation of given compounds, such as water.

With regards to the ageing step (b), it is preferably carried out by stirring the suspension prepared in step (a) using, for example, magnetic stirring (e.g. with a magnetic stirrer), and/or by mechanical stirring, and/or by shaking and/or by orbital stirring (e.g. using an orbital shaker).

The ageing step (b) is performed for at least 1 h. Ageing step (b) can preferably be performed for at least 2 h, and preferably for at least 8 hours.

In an embodiment, the stirring is performed by a magnetic stirrer for the first one hour, after the synthesis mixture has been completed in step (a). The suspension if-then transferred to an orbital shaker for an additional 18 h of mixing.

The ageing step (b) is preferably performed by maintaining the clear suspension prepared in step (a) at a relatively low temperature of about 10 to 35° C., preferably below 30° C. and even more preferably at a temperature of about 15 to 25° C. to prevent dehydration of the reaction mixture. The use of a sealed container is particularly preferred.

The ageing step (b) is preferably performed at a fixed temperature for a time sufficient to favour the nucleation, allowing each particle to generate a nucleus.

During the ageing step (b), the suspension remains homogeneous and leads to the formation of a suspension composed of homogeneous amorphous particles.

With regards to step (c), this step a hydrothermal treatment of the suspension obtained at the end of step (b) is performed. This step (c) leads to the formation of secondary building units and/or embryonic zeolites, and/or semi-crystalline zeolitic particles, and/or fully crystalline purely siliceous zeolitic particles; depending on the time and temperature of said hydrothermal treatment. This step is preferably performed to form colloidal suspensions of monodispersed zeolite nanocrystals or amorphous particles containing secondary building units.

Without willing to be bound to any theory, it is believed that in step (c), nuclei formed in step (b) grow to form secondary building units that rearrange themselves into embryonic zeolites, which stands as X-Ray amorphous species comprising secondary building units, and approaching zeolitic features such as rings and cages. These embryonic zeolites then rearrange themselves to form semi-crystalline products that are compounds formed from crystalline and still amorphous materials. These semi-crystalline units then are forming fully crystalline products, which are uniformly distributed in the solution (also called mother-liquor). If the crystallization temperature is too high, i.e. above 180° C., or if it is too low, i.e. below 40° C., bigger crystals or low crystallinity are achieved respectively.

Step (c) can be performed in both static conditions or in rotating autoclaves, but preferably in static conditions.

Step (c) can preferably be performed in sealed polypropylene bottle, at autogenous pressure preferably bellow 100° C., or in Teflon-lined autoclaves above 100° C.

Step (c) is advantageously performed without any agitation (i.e. without any mechanical stirring, or sonication).

Without willing to be bound to any theory, it is believed that the formation of homogeneous amorphous particles in step (b) drastically limits the Ostwald ripening of the nanocrystals formed, therefore insuring a narrow particle size distribution of the material in suspension.

At the end of step (c), the synthesis mixture can be composed of still fully amorphous material comprising secondary building units, or embryonic zeolites, and/or crystalline materials which are X-ray crystalline. The method being particularly versatile, a fully crystalline, free of amorphous material crystals can also be achieved. Depending on the case, the synthesis mixture can then be still water-clear, or turbid, milky, or composed of sedimented particles in mother-liquor. A milky suspension described here the aspect of the synthetic mixture, being a white liquid, like milk.

With regards to step (d), it consists in providing a solution or a gel at a temperature of 20 to 80° C., more preferably, down to about 20 to 50° C. followed by the addition of the alkali metal M'.

The gel obtained at step (c) can be directly used once the concentration of the various species is adapted to reach the composition (II).

The addition of the metal M and alkali metal M' can be either done under vigorous agitation, preferably performed by a magnetic stirrer, the addition of metals M and M' is performed.

The metals M and M' can be introduced for instance together, as fully dissolved species in water, preferably as a concentrated metallic aqueous solution.

All alkali metals can be used but the preferred alkali metals are Li or Na because with those alkali metals the synthesis is easier.

In a particularly advantageous embodiment, the sources of metal M and alkali metal M' are provided by the same component being a source of both M and M'. Such components are therefore alkali metallates such as $Na_2WO_4$, $K_2WO_4$, $NaVO_3$, $CsVO_3$, $LiVO_3$, $KVO_3$, $Na_2MoO_4$, $K_2MoO_4$, $Na_2SnO_3$, $K_2SnO_3$, or $Na_2ZrO_3$.

Alternatively, it is possible to provide M and M' separately. In that case, any source of M can be used as well as any source of M', as long as the mixture of the two in aqueous solution is at least partially soluble. The absence of M' from the synthesis mixture would result in the impossibility to introduce M in the zeolitic structures and would prevent the defect-healing process involving the metal M to occur. The presence of these M' alkali metal species is therefore of first importance for the method of the present disclosure to work out.

The overall synthetic mixture composition, after full addition of the metal M and M', is dissolved in water, is following the molar composition (II).

During the addition of metal species, the gel viscosity may dramatically change, and formation of precipitates may be observed.

With regards to step (e), it consists of an additional ageing step similar to the ageing step (b). This ageing step is preferably shorter than the ageing step (b). Preferably the duration of the ageing step (e) is 1 h, at a relatively low temperature ranging from 10 to 35° C. For example, the method of agitation is magnetic stirring.

The goal of this step is to achieve a homogeneous distribution of the metallic species in the synthetic mixture, or at least, a distribution as homogeneous as possible.

With regards to step (f), it consists of a hydrothermal treatment performed after step (e). The conditions of this second hydrothermal treatment step (f) can be the same as the conditions of step (c).

The temperature of hydrothermal treatment can be ranging from 40° C. to around 180° C. Most preferably, the same temperature is kept for step (c) and step (f).

Step (f) is preferably performed under autogenous pressure, in static conditions (i.e. without agitation).

The time of hydrothermal treatment is at least 30 min preferably at least 2 h, preferably at least 24 h, to allow metallic species to react with silanol defective sites, thus curing silanol defects in the zeolite, isomorphous substituting in the zeolitic material. Depending on the state of the material during step (e), it can be required to perform longer crystallization time to obtain fully crystalline material.

Depending on the state of the synthesis material in step (e), it is possible to obtain a different radial distribution of metals in the final product, based on the defective site locations in the material in step (e). Amorphous zeolitic materials have a homogeneous distribution of defective site, allowing for the homogeneous radial distribution of metal on final products, when crystalline materials tend to have higher amount defective sites in their periphery, allowing for a radial gradient of metal composition in the final product obtained at the end of the procedure of the present disclosure. After step (f), zeolite crystals are uniformly dispersed in the mother liquor and the particles are not agglomerated.

Without willing to be bound to any theory, it is believed that the delayed addition of metals M and M' at step (d), allows to prevent these metallic compounds from reacting and interfering with the nucleation process described in steps (a) and (b). As a result, the final particle size and morphology will be mostly dependent on the conditions of steps (a), (b), and (c), allowing for better management of particle size and morphology of the final products obtained at the end of the synthesis method of the present disclosure.

With regards to step (g), it consists in a separation and recovering step (i.e. purification and/or washing step) that can preferably be performed by filtration, centrifugation, dialysis, or by using flocculating agents followed by filtration, to separate and recover the solid (comprising the zeolite synthetic materials) from the mother-liquor.

The separation and recovering step (g) may advantageously be repeated at least two times, and preferably 5 times, with intermediate double distilled or de-ionized water addition to the solid particles, to purify the solid particles and remove any remnants from the mother-liquor that are materials that are not converted into zeolite material Separation and recovering step (g) are preferably performed using high-speed centrifugation.

Washes with water are preferentially performed until the remaining water (from washes) has a pH of about 7 to 8.

After step (g), the solid still contains the structure-directing agent which has been imprisoned into the zeolite cavities or channel system.

With regards to step (h), it consists of calcination. Once the solid is separated from the mother-liquor, at the end of step (g), it is submitted to calcination step (h) (i.e. heat treatment).

Step (h) is carried out at a temperature ranging from 400° C. to 800° C., for example, during 1 to 10 hours approximately, under a mixture of air, oxygen, an inert gas (such as nitrogen) and preferable in the presence of a small amount of water vapours (i.e. with a relative humidity of the gas used of about 1 to 5%).

The calcination step (h) aims to remove all the structure-directing agent still present in the zeolitic material obtained from step (g).

Without willing to be bound to any theory, it is believed that the thermal treatment does not degrade the structure of the zeolite material due to its high thermal stability achieved thanks to the defective sites healing performed by the metals M and M'.

It is also believed that to reduce the silanol species content of the zeolite material, some water vapours in the gas mixture used during the calcination step is particularly preferred.

Before calcination treatment of step (h), it is preferred to dry the sample. This drying step can be performed at 50 to 100° C., preferably at 80 to 90° C. The drying step is generally performed for 10 hours. A shorter duration of the drying step allowing to remove all the remaining water and allowing to obtain a powdered sample out of step (g) may also be used. In an embodiment, freeze-drying can also be performed to reduce drastically the chances of agglomerated particles. This is particularly preferred in case the drying step using a conventional oven yields to the formation of some agglomerates. Freeze-drying, or lyophilisation, is preferably performed at around −76 to −92° C., at sub-atmospheric pressure, for about 48 h.

With regards to optional further steps, the method can further comprise after step (h), an ion-exchange procedure in which alkali metal M' is removed from the zeolite, but metal M is kept. Such a procedure can be used in case the material is intended to be used as a catalyst in acidic catalysis. In this optional embodiment, the procedure is at it follows:

After the solid powder obtained at step (h) is added to an aqueous solution containing a salt of ammonium cation so that the alkali metal M' is replaced with ammonium. The ammonium salt used is preferably ammonium chloride ($NH_4Cl$), with a concentration of about 1.1 wt. % (0.02 M). For instance, 10 mL of a solution containing the ammonium is added for 100 mg of zeolite solid product from step (h). The procedure is preferably repeated twice with an intermediate separation procedure, best performed using centrifugation. The solid sample can then be retrieved and washed with water. The washing step is also performed preferably by using centrifugation. The ammonium salt used is preferably ammonium chloride ($NH_4Cl$), with a concentration of about 1.1 wt. % (0.02 M). For instance, 10 mL of a solution containing the ammonium is added for 100 mg of zeolite solid product from step (h). The procedure is preferably repeated twice with an intermediate separation procedure, best performed using centrifugation. The solid sample can then be retrieved and washed with water. The washing step is also performed preferably by using centrifugation.

The as-obtained material can then be dried and calcined according to the procedure described in step (h).

It is believed that this procedure may generate some isolated silanol species, but the amount of silanol generated by such procedure is still very low and far below any materials that would have been synthesized using a different approach than the approach described in the present disclosure.

The disclosure relates to a process for the conversion of methane into ethylene using a particular catalyst prepared according to the following steps:

a1) providing a synthetic zeolite material;
b1) optionally washing said synthetic zeolite material and drying it at a temperature of at least 50° C. for at least 2 h;
c1) optionally calcining at a temperature of at least 200° C. for at least 1 h the synthetic zeolite material obtained at step (a1) or at step (b1) if said step (b1) is carried out;
d1) putting said synthetic zeolite material in an aqueous solution comprising one source of alkali metal M' and at least one metal M wherein both M and M' are fully soluble in water and wherein the molar ratio M'/M is of at least 1 and the weight ratio of said synthetic zeolite over said clear solution is of at most 1000;
e1) optionally stirring the solution obtained at step (d1) for at least 30 min, preferably at room temperature and/or atmospheric pressure;
f1) heating the solution for at least 12 h and at a temperature of at least 50° C., preferably under autogenous pressure so that the solution does not evaporate;
g1) separating the liquid from the solid obtained at step (f1);
h1) drying the solid obtained at step (g1) and calcining it at a temperature of at least 200° C. for at least 1 h and recovering said catalyst.

In the embodiment where water is used as a solvent, de-ionized or double-distilled (dd $H_2O$) is preferred. As an example, double distillation can be performed as follows:

Tape-water is boiled, and the vapours are condensed in a clean container. The retrieved vapours are then boiled again, and retrieved in a second clean container. The as-obtained dd $H_2O$ can then be used.

With regards to step (d1), it consists in mixing said synthetic zeolite material at a temperature of 20 to 80° C., more preferably, of 20 to 50° C. with said clear solution comprising the metal M and the alkali metal M'. As a matter of example, 10 g of zeolite can be put in a 20 g of a clear solution containing the M+M'.

The addition of the metal M and the alkali metal M' in the solution can be performed simultaneously or the metal M can be added first followed by the alkali metal M'. Alternatively the alkali metal M' can be added first followed by the metal M. The metals M and M' can be introduced for instance together.

In the case M and M' are provided separately, any source of metal M can be used as well as any source of M', as long as the mixture of the two is soluble in the solution. For example, the solvent is water. The absence of M' from the synthesis mixture would result in the impossibility to introduce M in the zeolitic structures and would prevent the defect-healing process involving the metal M to occur. The presence of these M' alkali metal species is therefore of first importance for the process of the present disclosure to work out.

In a particularly advantageous embodiment, the sources of metal M and alkali metal M' are provided by the same component being a source of both M and M'. Such components are alkali metallates such as $Na_2WO_4$, $K_2WO_4$, $NaVO_3$, $CsVO_3$, $LiVO_3$, $KVO_3$, $Na_2MoO_4$, $K_2MoO_4$, $Na_2SnO_3$, $K_2SnO_3$, or $Na_2ZrO_3$.

With regards to the step (e1) and/or (f1), it is preferably carried out by stirring the solution prepared in step (d1) using, for example, magnetic stirring (e.g. with a magnetic stirrer), and/or by mechanical stirring, and/or by shaking and/or by orbital stirring (e.g. using an orbital shaker). In an embodiment, the stirring is performed by a magnetic stirrer during step (e1), after the synthesis mixture has been completed in step (d1). The suspension is then transferred to an orbital shaker for the additional mixing of step (f1). Alternatively, the step (e1) and/or (f1) can be performed under static conditions (i.e. without agitation).

The temperature of thermal treatment of step (f1) can be ranging from 60° C. to 120° C., preferably from 80 to 110° C., even more preferably from 90 to 100° C.

The duration of step (f1) is at least 12 h, preferably at least 24 h, even more preferably 72 h and preferably at most 96 h. The time of step (f1) should be long enough to allow metallic species to react with silanol defective sites, thus curing silanol defects in the zeolite, isomorphously substituting in the zeolitic material.

Without willing to be bound to any theory, it is believed that the addition of metals M and M' at step (d1) on an already formed zeolitic material instead of their incorporation during the synthesis process avoids that those metallic compounds interact with the nucleation process of the synthesis of the zeolite. As a result, the final particle size and morphology will be fixed during the synthesis of the zeolite and there will be no change during the incorporation of the metal M. There is, therefore, clear management of the particle size and morphology of the final products obtained at the end of the synthesis process of the present disclosure.

With regards to step (g1), it consists in a separation and recovering step (i.e. purification and/or washing step) that can preferably be performed by filtration, centrifugation, dialysis, or by using flocculating agents followed by filtration, to separate and recover the solid (comprising the defect-free zeolite synthetic materials) from the liquid.

The separation and recovering step (g1) may advantageously be repeated at least two times, and preferably 5 times, with intermediate double distilled or de-ionized water addition to the solid particles, to purify the solid particles.

Separation and recovering step (g1) are preferably performed using high-speed centrifugation. With regards to step (h1) and/or (c1), it consists in first a drying followed by calcination. Before calcination treatment of step (h1), the sample is dried. This drying step can be performed at 50 to 100° C., preferably at 80 to 90° C. The drying step is preferably performed for 12 hours. A shorter duration of the drying step allowing to remove all the remaining water and allowing to obtain a powdered sample out of step (g1) may also be used. In an embodiment, freeze-drying can also be performed to reduce drastically the chances of agglomerated particles. This is particularly preferred in case the drying step using a conventional oven yields to the formation of some agglomerates. Freeze-drying, or lyophilisation, is preferably performed at around −76 to −92° C., at sub-atmospheric pressure, for about 48 h.

Once the solid is separated from the liquid, at the end of step (g1), it is submitted to calcination step (h1) (i.e. heat treatment).

The calcination of step (h1) is carried out at a temperature of at least 200° C., preferably at a temperature ranging from 400° C. to 800° C., for example, during 1 to 10 hours approximately, under a mixture of air, oxygen, an inert gas (such as nitrogen) and preferably in the presence of a small amount of water vapours (i.e. with a relative humidity of the gas used of about 1 to 5%) to reduce the silanol species content on the zeolite material. The calcination of step (h1) is needed to achieve healing of the silanol defects by metal introduction on silanol sites. Without willing to be bound to any theory, it is believed that the thermal treatment does not degrade the structure of the zeolite material due to its high thermal stability achieved thanks to the defective sites healing performed by the metals M and M'.

The same considerations apply mutatis mutandis for the calcination of step (c1) whereas the calcination step (c1) aims to remove the organic template and to make the silanol sites easily accessible for metal incorporation.

With regards to optional further steps, the method can further comprise after step (h1), an ion-exchange procedure in which alkali metal M' is removed from the zeolite, but metal M is kept. Such a procedure can be used in case the material is intended to be used as a catalyst in acidic catalysis. In this optional embodiment, the procedure is at it follows:

After the solid powder obtained at step (h1) is added to an aqueous solution containing a salt of ammonium cation so that the alkali metal M' is replaced with ammonium.

The ammonium salt used is preferably ammonium chloride ($NH_4Cl$). For instance, a concentration of about 1.1 wt. % (0.02 M) of $NH_4Cl$ in water can be used. For instance, 10 mL of such a solution containing the ammonium can be added to 100 mg of zeolite solid product from step (h1) to proceed with the ion exchange. The procedure is preferably repeated at least twice with an intermediate separation procedure, best performed using centrifugation. The solid sample can then be retrieved and washed with water. The washing step is also performed preferably by using centrifugation.

The as-obtained material can then be dried and calcined according to the procedure described in step (h1).

It is believed that this procedure may generate some isolated silanol species, but the amount of silanol generated by such procedure is still very low and far below any materials that would have been synthesized using a different approach than the approach described in the present disclosure.

EXAMPLES

Nine examples of metal-containing MFI zeolite materials are described in the following section (one comparative example and examples 1 to 5):

The starting materials used in the examples are as follow:

Tetraehtylorthosilicate (TEOS), 98%, from Aldrich

Tetrapropylammonium hydroxyl (TPAOH), 20 wt. % in water (1 M), from Alfa Aesar

Sodium molybdate tetrahydrated ($Na_2MoO_4$, $2H_2O$), 98%, from Alfa Aesar

Ammonium hepta-molybdate (($NH_4$)$_6Mo_7O_{24}$), from Alfa Aesar

Sodium chloride (NaCl) from Alfa Aesar

Lithium, sodium, potassium, or caesium vanadate (Li, Na, K, $CsVO_3$) from Aldrich Sodium stannate ($Na_2SnO_3$), 95%, from Aldrich Double distilled water These materials were used as received from manufacturers without any further purification.

The zeolite samples described in the following examples are characterized by various methods as listed below:

Scanning Electron Microscopy (SEM):

Scanning electron microscopy images of examples after step (h) were recorded using a MIRA\LMH (TESCAN) microscope, with an electron beam of 30 kV.

Inductively coupled plasma (ICP) optical emission spectrometry was used to determine the chemical compositions using a Varian ICP-OES 720-ES. The Si/Al molar ratio or the Si/M molar ratio are determined using the said method.

Powder X-Ray Diffraction (XRD):

Powder samples of zeolites obtained after step (h) were measured using a PANalytical X'Pert Pro X-ray diffractometer equipped with a monochromator specific to CuKα radiation (λ=1.5418 Å, 45 kV, 40 mA). Samples were measured from 3 to 70° 2θ, with a step size of 0.016°.

Le Bail profile refinement of each XRD patterns was also performed.

Solid-State Nuclear Magnetic Resonance of Silicon ($^{29}$Si MAS NMR):

Powder samples obtained after step (h) are packed into zirconia rotor of 4 mm outer diameter spun at 12 kHz, in a Bruker Avance III-HD 500 (11.7 T) spectrometer operating at 99.3 MHz. $^{29}$Si MAS NMR spectra are recorded from a single pulse excitation (30° flip angle), used with a recycle delay of 30 s. {1H} $^{29}$Si cross-polarization (CP) solid-state MAS NMR was acquired using a contact time of 5 ms and a recycle delay of 2 s. Chemical shifts were referenced to tetramethyl silane (TMS).

Solid-State Nuclear Magnetic Resonance of Phosphorus ($^{31}$P MAS NMR):

Powdered sample obtained after step (h) and subsequently ion-exchanged to have the H-form, are analysed in $^{31}$P MAS NMR under $^1$H decoupling, using a phosphorus probe molecule: trimethylphosphine oxide (TMPO). All the following preparation steps are performed under Argon atmosphere to prevent interaction of water with the probe molecule. The sample is first dehydrated, by heating at 400° C. for 4 h under vacuum (av. 4.0×10$^{-5}$ Torr). In the meanwhile, a solution of TMPO dissolved in dichloromethane is prepared in anhydrous conditions. The solution is then added to the dehydrated sample. The as-obtained suspension is then subjected to sonication for 15 minutes, before the dichloromethane solvent is removed under vacuum, leaving the TMPO probe molecule impregnated into the zeolite sample. TMPO loaded sample is then packed into 4 mm outer-diameter zirconium rotor and analysed using $^{31}$P MAS NMR, performed on an 11.7 T Bruker Avance 500 spectrometer operating at a frequency of 500.0 MHz and 202.4 MHz for $^1$H and $^{31}$P respectively. A spinning rate of 14 kHz was used. $^{31}$P π/2 and π-pulses lengths were 7 and 14 μs respectively for all measurements.

Raman Spectroscopy:

Samples obtained after step (h) were measured using Raman spectrometry. The Raman spectra were collected on a Jobin Yvon Labram 300 confocal Raman spectrometer coupled to an optical microscope (objective 50×) and a CCD detector. A 532 nm wavelength laser was used, and spectra were accumulated 3 times for 60 s each. The power applied to the sample did not exceed 20 mW upon measurement.

Scanning Transmission Electron Microscopy with Energy Dispersive X-Ray Analysis (STEM/EDS) and High Angle Annular Dark Field Imaging (HAADF-STEM):

Experiments were performed on an Analytical double (objective and probe) corrected JEOL ARM2000F equipped with a 100 mm Centurio EDS detector and a Quantum GIF for the EELS. A probe of 0.1 nm was used to scan the sample in STEM mode and Bright Field and High Angle Annular Dark Field detectors were simultaneously employed for imaging. Camera length was 8 cm, and two different accelerating voltages of 200 and 80 kV were used in the STEM mode for imaging and chemical analysis respectively. Owing to the enhanced Z-contrast developed at 200 kV, this configuration was used for imaging and a high-speed scanning protocol (10 μsec/px) was employed to prevent sample degradation under the electron beam. To avoid such degradation, STEM-EDS analytical assays were carried out at 80 kV, with a scanning speed of 3 μs/px for a mean duration of 60 minutes. A cross-correlation algorithm implemented in the Jeol Analysis Station software was applied every 30 seconds in an effort to compensate for the special drift occurring during the test. The microstructure of samples was checked prior and after each EDS scan.

Catalytic Activity Testing

Before the catalytic test, the catalyst was pelletized, crashed and sieved to 200-400 μm particle size. Catalyst test was carried out in a quartz tubular reactor (367 mm long and 6.0 mm of internal diameter) loaded with 0.3 g of catalyst. To support the catalyst the quartz wool was used.

The catalytic experimental conditions for catalyst evaluation were: 1123 K, 1 bar, 1.22 h$^{-1}$. Before the reaction, the catalyst was activated by the temperature increase to reaction temperature with rate 10K/min in a flow of $CH_4/N_2$ (81/21 vol. %). An online gas Interscience CompactGC chromatograph equipped with three analysis channels was applied to analyze the products obtained. The GC configuration included 3 channels with 2 TCD, 1 FID detectors and different columns (Molsieve 5A, Rt-QBond, Rtx-1) for analysis of light gases, light hydrocarbons and aromatic hydrocarbons. Nitrogen was used as the internal standard. The main products of the reaction are hydrogen, ethylene, ethane, and aromatic products such as benzene, and/or toluene. The selectivity of naphthalene is less than 1.0%, preferably less than 0.5%, more preferably less than 0.1% or is equal to 0.0%. Indeed, the use of a synthetic zeolite material as the catalyst prevents the formation of naphthalene, since the pores of the catalyst are too small for letting naphthalene to be generated.

Comparative Example—SiMFI Zeolite

Preparation of Purely Siliceous Si-MFI Zeolite from the Same Gel Composition and Crystallization Method as Samples of the Present Disclosure. Note: This Sample is not Part of the Disclosure Step (a):

In a polypropylene synthesis bottle (125 mL), solution A is prepared by adding 24.591 g of TPAOH (1M) and 42.581 g of double-distilled water, under agitation performed using a magnetic stirrer. To this solution A is then added drop-wise 18 g of TEOS, under stirring performed by a magnetic stirrer. The solution should be water clear and liquid. Upon preparation, the gel might be slightly inhomogeneous, but the solution should end up being water-like during the ageing step (beginning of step (b)). The final overall molar gel composition (solution A and B mixed) is 1 SiO$_2$: 0.28 TPAOH: 40 H2O.

Step (b):

The bottle containing the solution prepared in step (a) is air-tightly closed with a cap. The as-made synthetic suspensions are left for ageing under magnetic stirring for 1 h, and then on an orbital shaker for an additional 18 h. All the steps up to this point are performed at a temperature between 10 and 35° C. and an ambient pressure between 0.9 and 1.2 Bar.

Step (c):

The synthesis mixture is water-like at this point. The synthetic mixture, still in its air-tightly closed bottle, is then subjected to static hydrothermal treatment at 90° C., for a duration of 48 h.

Step (d):

The sample is removed from the oven after step (c) and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step (e):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds at 550° C. for an additional 5 h, before the furnace is allowed to cool down to room temperature in 5 h. The as-obtained sample from step (e) is called SiMFI.

Example 1—MoMFI-1

Preparation of Molybdenum (Mo) Containing MFI Zeolite by Staged Synthesis Approach (Metal Source was Added to the Amorphous Material with a Delay of 5 h)

Step (a):

In a polypropylene synthesis bottle (125 mL), solution A is prepared by adding 8.197 g of TPAOH (1M) and 11.194 g of double-distilled water, under agitation performed using a magnetic stirrer. To this solution A is then added dropwise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic suspensions are left for ageing under magnetic stirring for 1 h, and then on an orbital shaker for an additional 18 h. All the steps up to this point are performed at a temperature between 10 and 35° C. and an ambient pressure between 0.9 and 1.2 Bar.

Step (c):

The synthesis mixture is water-like at this point. The synthetic mixture, still in its air-tightly closed bottle, is then subjected to static hydrothermal treatment at 90° C., for a duration of 5 h.

Step (d):

The synthesis bottle is retrieved from step (c), and cooled down to room temperature under magnetic agitation, without opening the bottle. The synthesis mixture inside is still fully amorphous at this stage of the synthesis method. A solution B is prepared from 0.553 g of sodium molybdate di-hydrated Na$_2$MoO$_4$.2H$_2$O dissolved in 3 mL of double-distilled water. The solution is hand-shaken until it becomes water-clear. Solution B is then added drop-wise to the mixture that has just been cooled down, under vigorous magnetic stirring.

Step (e):

After full addition of the metal source, the bottle is closed again and left under magnetic stirring for an additional 1 h. The final overall molar gel composition (solution A and B mixed) is 1 SiO$_2$:0.28 TPAOH:0.08 MoO$_3$:0.08 M'$_2$O:40 H2O.

Step (f):

The obtained synthesis mixture from step (e) is then placed in a static oven at 90° C. for 43 h.

Step (Q):

The sample is removed from the oven after step (e) and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds at 550° C. for an additional 5 h, before the furnace is allowed to cool down to room temperature in 5 h. The as-obtained sample from step (h) is called MoMFI-1.

Example 2—MoMFI-2

Preparation of Molybdenum (Mo) Containing MFI Zeolite by Staged Synthesis Approach (Metal Source was Added to the Fully Crystalline Material with a Delay of 48 h)

Step (a):

In a polypropylene synthesis bottle (125 mL), solution A is prepared by adding 8.197 g of TPAOH (1M) and 11.194 g of double-distilled water, under agitation performed using a magnetic stirrer. To this solution A is then added drop-wise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic gel is left for ageing under magnetic stirring for 1 h, and then on an orbital shaker for an additional 18 h. All the steps up to this point are performed at a temperature between 10 and 35° C. and an ambient pressure between 0.9 and 1.2 Bar.

Step (c):

The synthesis mixture is water-like at this point. The synthetic gel, still in its air-tightly closed bottle, is then subjected to static hydrothermal treatment at 90° C., for a duration of 48 h.

Step (d):

The synthesis bottle is retrieved from step (c), and cooled down to room temperature under magnetic agitation, without opening the bottle. The mixture inside is composed of purely siliceous fully crystalline MFI zeolite in its mother-liquor. A solution B is prepared from 0.553 g of sodium molybdate $Na_2MoO_4 \cdot 2H_2O$ dissolved in 3 mL of double-distilled water. The solution is hand-shaken until it becomes water-clear. Solution B is then added drop-wise to the mixture that has just been cooled down, under vigorous magnetic stirring.

Step (e):

After full addition of the metal, the synthesis bottle is closed again and left under magnetic stirring for an additional 1 h. The final overall molar gel composition (solution A and B mixed) is 1 $SiO_2$: 0.28 TPAOH: 0.08 $MoO_3$: 0.08 $M'_2O$:40 $H_2O$.

Step (f):

The obtained synthesis mixture from step (e) is then placed in a static oven at 90° C. for 24 h.

Step (g):

The sample is removed from the oven after step (e) and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step (h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds the temperature at 550° C. for an additional 5 h before the furnace is allowed to cool down to room temperature in 5 h. The as-obtained sample from step (h) is called MoMFI-2.

Example 3—SnMFI

Preparation of Tin (Sn) Containing MFI Zeolite by Staged Synthesis Approach (Metal Source was Added to the Amorphous Material with a Delay of 5 h)

Step (a):

In a polypropylene synthesis bottle (125 mL), solution A is prepared by adding 8.197 g of TPAOH (1M) and 11.194 g of double-distilled water, under agitation performed using a magnetic stirrer. To this solution A is then added drop-wise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic gel is left for ageing under magnetic stirring for 1 h, and then on an orbital shaker for an additional 18 h. All the steps up to this point are performed at room temperature and ambient pressure.

Step (c):

The synthesis mixture is water-like at this point. The synthetic gel, still in its air-tightly closed bottle, is then subjected to static hydrothermal treatment at 90° C., for a duration of 5 h.

Step (d):

The synthesis bottle is retrieved from step (c), and cooled down to room temperature under magnetic agitation, without opening the bottle. The synthesis mixture inside is still fully amorphous at this stage of the synthesis method. A solution B is prepared from 0.461 g of sodium stannate tri-hydrated $Na_2SnO_3 \cdot 3H_2O$ dissolved in 3 mL of double-distilled water. The solution is hand-shaken until it becomes water-clear. Solution B is then added dropwise to the mixture that has just been cooled down, under vigorous magnetic stirring.

Step (e):

After full addition of the metal, the synthesis bottle is closed again and left under magnetic stirring for an additional 1 h. The final overall molar gel composition (solution A and B mixed) is 1 $SiO_2$:0.28 TPAOH:0.06 $SnO_3$: 0.06 $M'_2O$:40 $H_2O$.

Step (f):

The obtained synthesis mixture from step (e) is then placed in a static oven at 90° C. for 43 h.

Step (g):

The sample is removed from the oven after step (e) and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step (h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds the temperature at 550° C. for an additional 5 h before the furnace is allowed to cool down to room temperature in 5 h. The as-obtained sample from step (h) is called SnMFI.

Example 4—MoMFI-4

Preparation of Molybdenum (Mo) Containing MFI Zeolite by Staged Synthesis Approach (Metal Sources (M and M') were Added to the Amorphous Material with a Delay of 5 h)

Step (a):

In a polypropylene synthesis bottle (125 mL), solution A is prepared by adding 8.197 g of TPAOH (1M) and 11.191 g of double-distilled water, under agitation performed using a magnetic stirrer. To this solution A is then added drop-wise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic gel is left for ageing under magnetic stirring for 1 h, and then on an orbital shaker for an additional 18 h. All the steps up to this point are performed at room temperature and ambient pressure.

Step (c):

The synthesis mixture is water-like at this point. The synthetic gel, still in its air-tightly closed bottle, is then subjected to static hydrothermal treatment at 90° C., for a duration of 5 h.

Step (d):

The synthesis bottle is retrieved from step (c), and cooled down to room temperature under magnetic agitation, without opening the bottle. The synthesis mixture inside is still fully amorphous at this stage of the synthesis method. A solution B is prepared from 0.305 g of ammonium heptamolybdate tetra-hydrated $(NH_4)_6Mo_7O_{24}.4H_2O$, and 0.202 g of sodium chloride dissolved in 3 mL of double-distilled water. The solution is hand-mixed until it becomes water-clear. Solution B is then added drop-wise to the mixture that has just been cooled down, under vigorous magnetic stirring.

Step (e):

After full addition of the metal, the synthesis bottle is closed again and left under magnetic stirring for an additional 1 h. The final overall molar gel composition (solution A and B mixed) is 1 $SiO_2$:0.28 TPAOH:0.06 $MoO_3$:40 $H_2O$:0.12 NaCl.

Step (f):

The obtained synthesis mixture from step (e) is then placed in a static oven at 90° C. for 43 h.

Step (g):

The sample is removed from the oven after step (e) and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step (h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds the temperature at 550° C. for an additional 5 h before the furnace is allowed to cool down to room temperature in 5 h. The as-obtained sample from step (h) is called MoMFI-3.

Example 5—VMFI-1 to VMFI-5

Synthesis of Vanadium (V) Containing MFI Zeolite by Staged Synthesis Approach, Using Different Alkali Metals (Metal Source was Added to the Amorphous Material with a Delay of 5 h).

Step (a):

In a polypropylene synthesis bottle (125 mL), solution A is prepared by adding 8.197 g of TPAOH (1M) and 11.194 g of double-distilled water, under agitation performed using a magnetic stirrer. To this solution A is then added drop-wise 6 g of TEOS, under stirring performed by a magnetic stirrer. The solution should be water clear and liquid. Upon preparation, the gel might be slightly inhomogeneous, but the solution should end up being water-like during the ageing step (beginning of step (b)).

Step (b):

The bottle containing the solution prepared in step (a) is air-tightly closed with a cap. The as-made synthetic gel is left for ageing under magnetic stirring for 1 h, and then on an orbital shaker for an additional 18 h. All the steps up to this point are performed at room temperature and ambient pressure.

Step (c):

The synthesis mixture is water-like at this point. The synthetic gel, still in its air-tightly closed bottle, is then subjected to static hydrothermal treatment at 90° C., for a duration of 5 h.

Step (d):

The synthesis bottle is retrieved from step (c), and cooled down to room temperature under magnetic agitation, without opening the bottle. The synthesis mixture inside is still fully amorphous at this stage of the synthesis method. A solution B is prepared from 0.183 g of lithium vanadate or 0.211 g of sodium vanadate or 0.239 g of potassium vanadate, or 0.401 g of caesium vanadate ($CsVO_3$), dissolved in 3 mL of double-distilled water. The solution is hand-shaken until it becomes water-clear. Solution B is then added drop-wise to the mixture that has just been cooled down, under vigorous magnetic stirring.

Step (e):

After full addition of the metal, the synthesis bottle is closed again and left under magnetic stirring for an additional 1 h. The final overall molar gel composition (solution A and B mixed) is 1 $SiO_2$:0.28 TPAOH:0.03 $V_2O_5$:0.03 $M'_2O$:40 $H_2O$.

Step (f):

The obtained synthesis mixture from step (e) is then placed in a static oven at 90° C. for 43 h.

Step (g):

The sample is removed from the oven after step (e) and cooled down to room temperature.

The solid phase is then separated from the liquid phase using centrifugation. The solid is dispersed in distilled water and centrifugation is performed again. This washing procedure is repeated until the pH of the liquid separated from the solid phase is around 7-8.

Step (h):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds the temperature at 550° C. for an additional 5 h before the furnace is allowed to cool down to room temperature in 5 h. The as-obtained sample from step (g) is called VMFI-1 in case lithium vanadate was used in step (d); VMFI-2 for sodium vanadate; VMFI-3 for potassium vanadate; and VMFI-4 for caesium vanadate.

Example 6

Preparation of Molybdenum (Mo) Containing Silicalite-1 Zeolite with a Fully Crystalline, Purified and Calcined Sample as Starting Material The steps 1) to 4) correspond to the normal synthesis of the Silicalite-1 zeolite. The steps 5) to 10) correspond to the isomorphous substitution of the MFI with molybdenum.

Step 1):

In a polypropylene synthesis bottle (125 mL), solution A is prepared by adding 24.591 g of TPAOH (1M) and 42.581 g of double-distilled water, under agitation performed using a magnetic stirrer. To this solution A is then added drop-wise 18.0 g of TEOS, under stirring performed by a magnetic stirrer. The solution should be water clear and liquid. Upon preparation, the gel might be slightly inhomogeneous, but the solution should end up being water-like during the ageing process (beginning of step 2). The molar composition of the as-prepared precursor suspension is the following: 0.28 TPAOH:1 $SiO_2$:40 $H_2O$ Step 2):

The bottle containing the solution prepared in step 1) is air-tightly closed with a cap. The as-made synthetic suspensions are left for ageing under magnetic stirring for 1 h, and then on an orbital shaker (225 rpm) for an additional 18 h. All the process up to this point is performed at room temperature and ambient pressure.

Step 3):

The synthesis mixture is water-like at this point. The synthetic mixture, still in its air-tightly closed bottle, is then subjected to static hydrothermal treatment at 90° C., for a duration of 48 h.

Step 4):

The sample is removed from the oven after step 3), and cooled down to room temperature. The solid phase is then separated from the liquid phase using centrifugation. The solid is dispersed in distilled water and centrifugation is performed again. This washing procedure is repeated until the pH of the liquid separated from the solid phase is around 7-8.

Step 5) correspond to step b1) and c1):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds at 550° C. for an additional 5 h, before the furnace is allowed to cool down to room temperature in 5 h.

Step 6):

300 mg of the obtained purely siliceous and fully crystalline Silicalite-1 zeolite that was calcined in step 5), is then introduced in a sealed container containing a solution composed by 0.208 g of sodium molybdate ($Na_2MoO_4.2H_2O$) dissolved in 8.0 g of distilled water.

Step 7) (corresponds to step e1):

The obtained suspension is mixed with a magnetic stirrer for 1 h at room temperature.

Step 8) (corresponds to step f1):

The obtained suspension from step 7) is then placed in a static oven at 90° C. for 96 h.

Step 9) (corresponds to step g1):

The sample is removed from the oven after step 8), and cooled down to room temperature. The solid phase is then separated from the liquid phase using centrifugation. The solid is dispersed in distilled water and centrifugation is performed again. This washing procedure is repeated several times (around 3 to 6 times) to remove any unreacted species.

Step 10) (corresponds to step (h1)):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds at 550° C. for an additional 5 h, before the furnace is allowed to cool down to room temperature in 5 h. The as-obtained sample from step 8) is called Mo-Silicalite-1.

After step 10) the Mo-containing nanosized materials were ion-exchanged with a solution of 0.2 M of $NH_4Cl$ (1 h at 25° C.), washed with dd $H_2O$ and calcined at 550° C. to eliminate the $NH_3$ and obtain the zeolite nanocrystals in acidic form. This procedure was repeated twice. After this procedure, the sample obtained is named Sample 1.

Example 7

Preparation of Molybdenum (Mo) Containing ZSM-5 Zeolite with a Fully Crystalline, Purified and Calcined ZSM-5 Zeolite as Starting Material (Sample Mo-ZSM-5)

The steps 1) to 4) correspond to the synthesis of the ZSM-5 zeolite. The steps 5) to 10) correspond to the isomorphous substitution of the ZSM-5 with molybdenum.

Step 1):

In a polypropylene bottle (125 mL), solution A is prepared by adding 41.804 g of TPAOH (1M) and 0.346 g of aluminum nitrate ($Al(NO_3)_3$, $9H_2O$), under agitation using a magnetic stirrer until complete dissolution of the salt. To this solution A is then added drop-wise 24.0 g of TEOS, under stirring using a magnetic stirrer. The solution becomes water clear after 30 min (beginning of step 2). The molar composition of the as-prepared precursor suspension is the following: 0.357 TPAOH:0.004 $Al_2O_3$:1 $SiO_2$:16.189 $H_2O$ Step 2):

The bottle containing the precursor suspension prepared in step 1) is air-tightly closed with a cap. The as-made synthetic suspensions are left for ageing on a magnetic stirrer for 1 h, and then on an orbital shaker for an additional 18 h (225 rpm). All the process up to this point is performed at room temperature and ambient pressure.

Step 3):

The precursor suspension is water-like at this point. Then it is transferred into Teflon-lined autoclaves, and subjected to static hydrothermal treatment at 180° C., for a duration of 72 h.

Step 4):

The sample is removed from the oven after step 3), and cooled down to room temperature.

The solid phase is then separated from the liquid phase using centrifugation. The solid is dispersed in distilled water after reaching the pH of the liquid separated from the solid phase of 7-8.

Step 5):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace and heated at 550° C. in 5 h, holds at 550° C. for an additional 5 h and cooled down to room temperature in 5 h. The ZSM-5 zeolite has a Si/Al ratio of 112 based on ICP analysis.

Step 6):

1.2 g of the fully crystalline calcined ZSM-5 zeolite (after step 5), is then introduced in a sealed container containing a solution composed by 0.800 g of sodium molybdate ($Na_2MoO_4.2H_2O$) dissolved in 25 mL of double-distilled water.

Step 7):

The obtained suspension is mixed with a magnetic stirrer for 1 h at room temperature.

Step 8):

The obtained suspension from step 7) is then placed in a static oven at 90° C. for 9 days.

Step 9):

The sample is removed from the oven after step 8), and cooled down to room temperature. The solid phase is then separated from the liquid phase using centrifugation. The solid is dispersed in distilled water and purified by centrifugation again. This washing procedure is repeated several times (3 to 6 times) to remove any unreacted species.

Step 10):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace and heated at 550° C. in 5 h, holds at 550° C. for an additional 5 h and cooled down to room temperature in 5 h. The as-obtained sample from step 8) is called Mo-ZSM-5.

Characterizations of Mo-Silicalite-1 and Mo-ZSM-5 Samples:

The XRD pattern together with the $^{29}$Si MAS NMR spectra of samples Mo-Silicalite-1 and Mo-ZSM-5 show that Mo is perfectly substituted on the MFI structure.

The $^1$H MAS NMR of dehydrated zeolite samples allows calculating a ratio of the concentration of surface OH when Mo is present or not. It appears that the ratios are the following:

$n$OH(Silicalite-1)/$n$OH(Mo-Silicalite-1)=3.6

$n$OH(ZSM-5)/$n$OH(Mo-ZSM-5)=2.8

There is consequently respectively 3.6 and 2.8 OH groups in the initial Mo free samples for every OH groups in the corresponding Mo-containing sample.

Example 8

Preparation of a Comparative Example by Classical Impregnation of a ZSM-5 with Mo Mo-containing ZSM-5 catalyst was prepared via impregnation of the required amount of ammonium heptamolybdate solution onto H-form of ZSM-5 catalyst with Si/Al ratio of 25 via incipient wetness, followed by drying at 393 K for 3 hours and calcination at 823 K for 6 hours in flowing air. Nominal molybdenum loading (wt. % of metal-based on the total weight of the catalyst) was targeted at 3 wt. %.

Before the catalytic test, the above material was ion-exchanged with a solution of 0.2M of NH$_4$Cl (1 h at 25° C.), washed with dd H$_2$O and calcined at 550° C. to eliminate the NH$_3$ and obtain the zeolite nanocrystals in acidic form. This procedure was repeated twice. The sample hence obtained is named sample 3.

Example 9

This example is very similar to example 7 apart from that the starting material was a commercial zeolite ZSM-5 supplied by Zeolyst (CBV CBV 5524G) as for comparative sample 3.

Step 1):

The commercial zeolite ZSM-5 Si/Al=25 supplied by Zeolyst company in ammonia form was subjected to the following calcination procedure: In ambient atmospheric conditions (the composition of the atmosphere, and atmospheric pressure), the sample is placed in a muffle furnace and heated at 550° C. in 5 h, holds at 550° C. for an additional 5 h and cooled down to room temperature in 5 h.

Step 2):

1.2 g of calcined ZSM-5 zeolite (after step 1), is then introduced in a sealed container containing a solution composed by 0.800 g of sodium molybdate (Na$_2$MoO$_4$.4H$_2$O) dissolved in 25 mL of double-distilled water.

Step 3):

The obtained suspension is mixed with a magnetic stirrer for 1 h at room temperature.

Step 4):

The obtained suspension from step 3) is then placed in a static oven at 90° C. for 9 days.

Step 5):

The sample is removed from the oven after step 4), and cooled down to room temperature. The solid phase is then separated from the liquid phase using centrifugation. The solid is dispersed in distilled water and purified by centrifugation again. This washing procedure is repeated several times (3 to 6 times) to remove any unreacted species.

Step 6):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace and heated at 550° C. in 5 h, holds at 550° C. for an additional 5 h and cooled down to room temperature in 5 h. The as-obtained sample from step 8) is called Mo-ZSM-5.

Step 7)

Prior the catalytic test the Mo-containing nanosized materials were ion-exchanged with a solution of 0.2M of NH$_4$Cl (1 h at 25° C.), washed with dd H$_2$O and calcined at 550° C. to eliminate the NH$_3$ and obtain the zeolite nanocrystals in acidic form. This procedure was repeated twice. The sample obtained is hence named sample 2.

Example 10

Step 1):

A clear aqueous silicate suspension A was prepared by mixing 12 g of TEOS with 16.4 g of TPAOH (20% solution in water). The clear aqueous silicate suspension A was stirring at room temperature (i.e. 25° C.).

A clear aqueous suspension B was prepared by mixing 1.1 g of sodium molybdate dehydrate (Na$_2$MoO$_4$.2H$_2$O) in 28.2 of dd H$_2$O.

Suspension B was added dropwise to the suspension A. During the addition, suspension A was maintained at room temperature while being vigorously stirred. The pH of the resulting clear aqueous suspension was about 12.

The resulting clear aqueous suspension had the following molar composition:

$$0.08MoO_3:SiO_2:0.28TPA_2O:0.08Na_2O:40H_2O \qquad (I).$$

Step 2):

The resulting clear aqueous suspension was then aged by magnetic stirring for 3 hours at room temperature and by orbital stirring for 14 hours at room temperature.

Step 3):

Then, the hydrothermal crystallization was conducted at 90° C. for 48 hours.

Step 4):

The solid was separated and recovered by high-speed centrifugation (20000 rpm, 10 min) and several washes with hot double distilled water (heated at 100° C. for 30 min) until the pH of the remaining water was about 7.5.

Step 5):

The obtained solid sample is then dried in a static oven at 80° C. overnight.

The dried sample retrieved is then subjected to the following calcination procedure: In ambient atmospheric conditions (the composition of the atmosphere, and atmospheric pressure), the sample is placed in a muffle furnace. The furnace heats up from room temperature to 550° C. in 5 h, holds at 550° C. for an additional 5 h, before the furnace is allowed to cool down to room temperature in 5 h.

Step 6)

Prior the catalytic test the Mo-containing nanosized materials were ion-exchanged with a solution of 0.2M of NH$_4$Cl (1 h at 25° C.), washed with dd H$_2$O and calcined at 550° C. to eliminate the NH$_3$ and obtain the zeolite nanocrystals in acidic form. This procedure was repeated twice. The sample hence obtained is named sample 4.

Catalyst Testing

The catalyst tests demonstrate the particularity of product distribution in methane to ethylene over the synthetic metal-containing zeolite material. As shown in Table 4 the catalytic behaviour of Samples 1, 2, 4 is characterized by a high contribution of C2 hydrocarbons.

The selectivity to C2 hydrocarbons for Sample 2 is above 55% during the whole experiment. Pure silica materials (Samples 1 and 4) produce almost only C2 hydrocarbons and no aromatics.

It is indeed known that aromatics are coke precursors. If aromatics are produced in large quantities, the catalyst also deactivates quickly due to the formation of coke. Consequently, the low production of aromatics in the case of sample 2 and in the case of samples 1 and 4 are particularly advantaging. Those catalysts will be very resistant to coking.

On the other hand, the comparative sample 3 shows a high production of aromatics followed by a rapid deactivation.

Table 4 also demonstrates the stability of catalyst activity and selectivity to C2 hydrocarbons in continuous cycles of reaction-regeneration.

After the catalytic reaction, the reactor with the Sample 1 was cooled down to room temperature in nitrogen flow of 10 ml/min followed by regeneration of catalyst in the same reactor in airflow of 15 ml/min. The regeneration procedure included a gradual increase in temperature up to 1023 K with a rate of 2 K/min and standing at this temperature for 3 h.

It is clear from Table 4 that continuous cycles of reaction regeneration do not affect catalyst activity and selectivity to C2 hydrocarbons.

Indeed, the regeneration of a traditional catalyst like sample 3 leads to the deactivation of the catalyst. Mo is only deposited on the surface of the support, during regeneration, there is the formation of $MoAl_2O_4$ inactive for the reaction. There is, therefore, a clear advantage in having Mo grafted in the structure of the support: during regeneration, Mo does not form inactive species and the catalyst stay active even after regeneration.

The catalysts of the present disclosure present therefore two advantages: they are selective toward C2 hydrocarbons and they are stable during the regeneration.

The FIGS. 19 and 20 show the stability of the Sample 2 catalyst in terms of activity and selectivity to hydrocarbons in time-on-stream as compared with the Sample 3 prepared by conventional incipient wetness impregnation of molybdenum onto ZSM-5 catalyst. The catalytic results show (FIG. 19, FIG. 20, and Table 4) that Sample 3 deactivates much faster than Sample 2. Moreover, Sample 2 is characterized by steady-state production of C2 hydrocarbons at at least 250 min of the experiment. At the same time, the comparative Sample 3 suffers from rapid catalyst deactivation with a corresponding decrease of C2 hydrocarbons production already after the first 75 minutes of the experiment.

The C2 fraction contains always at least 95% of ethylene. The activity of the metal-containing zeolites could be fully recovered by regeneration. The metal after regeneration remained in the structure. These materials demonstrate high stability vs time-on-stream relative to the catalyst of the same composition, containing the same zeolite by prepared by impregnation.

TABLE 4

The catalytic performance of catalysts in methane non-oxidative coupling reaction. 1123 K, 1 bar, 1.22 h$^{-1}$ (the data are given on coke-free basis).

| TOS, min | Methane conversion (%) | Selectivity to C2 + C2 = (%) | Selectivity to aromatics (%) |
|---|---|---|---|
| Sample 1 (Mo-Silicalite-1 zeolite), 1$^{st}$ run | | | |
| 50 | 1.2 | 99.4 | 0.6 |
| 100 | 1.4 | 99.7 | 0.3 |
| 200 | 2.1 | 99.8 | 0.2 |
| 400 | 2.2 | 99.9 | 0.1 |
| 600 | 2.3 | 99.9 | 0.1 |
| 800 | 2.5 | 99.9 | 0.1 |
| 1000 | 2.5 | 99.9 | 0.1 |
| Sample 1, 2$^{nd}$ run | | | |
| 50 | 1.3 | 99.6 | 0.4 |
| 100 | 1.5 | 99.9 | 0.1 |
| 200 | 2.2 | 99.9 | 0.1 |
| 300 | 2.2 | 99.9 | 0.1 |
| Sample 1, 3$^{rd}$ run | | | |
| 50 | 1.2 | 99.2 | 0.8 |
| 100 | 1.6 | 99.9 | 0.1 |
| 200 | 2.3 | 99.9 | 0.1 |
| 300 | 2.3 | 99.9 | 0.1 |
| Sample 2 (Mo- ZSM-5) | | | |
| 50 | 6.0 | 55.6 | 44.4 |
| 100 | 7.3 | 55.0 | 44.6 |
| 150 | 7.2 | 57.0 | 43.0 |
| 200 | 7.1 | 64.5 | 35.5 |
| 250 | 7.1 | 71.3 | 28.7 |
| 300 | 6.2 | 76.8 | 23.2 |
| Sample 3 (comparative: ZSM-5 impregnated with Mo) | | | |
| 50 | 17.3 | 18.0 | 82.0 |
| 100 | 10.4 | 83.8 | 16.2 |
| 150 | 4.1 | 96.1 | 3.9 |
| 200 | 3.3 | 99.4 | 0.6 |
| 250 | 3.2 | 99.7 | 0.3 |
| 300 | 3.3 | 99.7 | 0.3 |
| Sample 4 (Mo-Silicalite-1 zeolite) | | | |
| 50 | 1.6 | 98.2 | 1.8 |
| 100 | 1.7 | 99.1 | 0.9 |
| 200 | 2.0 | 99.6 | 0.4 |
| 400 | 2.0 | 99.8 | 0.2 |
| 600 | 2.2 | 99.8 | 0.2 |
| 800 | 2.3 | 99.9 | 0.1 |
| 1000 | 2.3 | 99.9 | 0.1 |

Selectivity to Naphthalene

Example 9 of WO2014/183337 is reported here as a further comparative example.

The catalyst used is a 1.5 g 0.5 wt. % oNi-0.5 wt. %)Co@SiO2catalyst prepared by vapor phase deposition. The catalyst was loaded in the fix-bed reactor, and then purged by Ar gas (25 ml/min) for 20 mins. Maintaining a constant flow rate of Ar, the reactor is programmed from room temperature up to 750° C. at a heating rate of 10° C./min. And then the weight hourly space velocity (WHSV) of feed gas was adjusted to 1600 ml/g/h. The results of methane conversion and products selectivity were as follows:

TABLE 5

| | | methane conversion for Example 9 of WO2014/183337 | | | |
|---|---|---|---|---|---|
| Temperature (° C.) | WHSV (ml/g/h) | Methane conversion (%) | Ethylene selectivity (%) | Benzene selectivity (%) | Naphtalene selectivity (%) |
| 750 | 1600 | 2.2 | 68 | 16 | 16 |

WHSV = weight hourly space velocity

From the results it can be seen that the selectivity to naphthalene is 16%. By contrast, the selectivity to naphthalene is very low with the catalyst of the disclosure (i.e. less than 1%) since the pores of the zeolite material used are too small for letting naphthalene to be generated.

The low selectivity to naphtalene is an advantage since it allows a reduction of the coke formed at high temperature and therefore allows working at higher temperatures.

The invention claimed is:
1. Process for the conversion of methane into ethylene and hydrogen, under non-oxidative conditions, comprising:
   i. providing a first stream containing at least 50 vol. % of methane based on the total volume of the said first stream;
   ii. providing a catalyst;
   iii. putting in contact said first stream with said catalyst at a weight hour space velocity ranging from 0.5 to 100 h$^{-1}$, at a temperature ranging from 8000 to 1100° C. and at a pressure ranging from 0.1 MPa to 5.0 MPa, and in the absence of oxygen; and
   iv. recovering a second stream containing unconverted methane if any, ethylene and hydrocarbons having at least 2 carbon atoms;
   characterized in that said catalyst is a synthetic zeolite material, containing at least one metal M with silicon to metal M molar ratio Si/M ranging from 100 to 65440 as determined by inductively coupled plasma optical emission spectrometry, in that said metal M is incorporated inside of the zeolite tetrahedral sites and in that metal M is selected from V, Mo, and any mixture thereof.
2. The process according to claim 1, characterized in that the temperature in step (iii) is ranging from 820 to 1000° C.
3. The process according to claim 1, characterized in that said catalyst is pre-treated at step (ii) with a third stream containing CO, $CO_2$, $C_2H_4$, $C_2H_6$, $H_2O$, or C3+ hydrocarbon mixture containing at least 10 wt. % of acyclic hydrocarbons, or a mixture of thereof.
4. The process according to claim 1, characterized in that said synthetic zeolite material is selected from the group of MOR, MWW, EUO, TON, MTT, CHA, MEL, MFI, BEA and/or FAU families.
5. The process according to claim 1, characterized in that said synthetic zeolite material is selected from the group of MWW, MFI, BEA and/or FAU families.
6. The process according to claim 1, characterized in that said synthetic zeolite material contains no aluminium or contains aluminium with a molar ratio Si/Al from 5 to 2000 as determined by inductively coupled plasma optical emission spectrometry.
7. The process according to claim 1, characterized in that said synthetic zeolite material comprises a content of 0.1 to 10 wt. % of metal M based on the total mass of the synthetic zeolite material measured according to EDS-TEM.
8. The process according to claim 1, characterized in that said synthetic zeolite material has a specific surface area ranging from 300 to 500 m$^2$/g measured according to the BET method ASTM D3663-03.
9. The process according to claim 1, characterized in that said synthetic zeolite material has a pore volume from 0.1 to 0.7 cm$^3$/g measured according to the BET method ASTM D3663-03.
10. The process according to claim 1, characterized in that said synthetic zeolite material has an external surface area from 10 to 190 m$^2$/g measured according to the BET method ASTM D3663-03.
11. The process according to claim 1, characterized in that said metal M is Mo.
12. The process according to claim 1, characterized in that said synthetic zeolite material is prepared according to the following steps:
   a) contacting at least one source of silicon, at least one tetra-alkylammonium hydroxide structure-directing agent, and water, to obtain an aqueous suspension having the following molar composition (I):

$1SiO_2:yTAA_2O:zH_2O$ in which: $0.04 < y < 0.40$,
   $8 < z < 120$,
   b) ageing during a time ranging between 1 h and 100 h the resulting aqueous suspension from step (a) at a temperature ranging from 10° C. to 50° C., to obtain an aged aqueous suspension;
   c) heating for at least 30 min the aged aqueous suspension of step (b) at a temperature ranging from 40° C. to 180° C., to obtain a solution;
   d) cooling the solution obtained at step (c) to 20° C., adding at least one source of alkali metal M' and at least one source of metal M, to obtain a gel having the molar composition (II):

$xM_nO_m:1SiO_2:yTAA_2O:wM'_2O:zH_2O$ in which: the M'/M ratio varies from 0.1 to 4,
   $0.04 < y < 0.40$,
   $8 < z < 120$,
   $0.0004 < x < 0.15$,
   $0.0004 < w < 0.30$,
   n is an integer equal to 1 or 2, and
   m is an integer and $1 < m < 6$;
   e) ageing said gel obtained at step (d) at a temperature ranging from 10° C. to 35° C. for at least 30 min;
   f) heating the solution obtained at step (e) at a temperature ranging from 40° C. to 180° C., for at least 30 min and at most 96 h;
   g) separating the solid from said liquid obtained at step (f);
   h) calcining said solid obtained at step (g) to obtain said synthetic zeolite material.
13. The process according to claim 12, characterized in that said at least one source of silicon of step (a) is selected from silica hydrogel, silicic acid, colloidal silica, fumed silica, tetraalkyl orthosilicates, silica hydroxides, precipitated silica and sodium silicates; and/or said at least one tetra-alkylammonium hydroxide structure-directing agent of step (a) is selected from tetraethylammonium hydroxide, tetrabutylammonium hydroxide or tetrapropylammonium hydroxide.
14. The process according claim 1, characterized in that said catalyst is prepared according to the following steps:
   a1) providing a synthetic zeolite material;
   b1) optionally, washing said synthetic zeolite material and drying it at a temperature of at least 50° C. for at least 2 h;

c1) optionally, calcining at a temperature of at least 200° C. for at least 1 hour the synthetic zeolite material obtained at step (a1) or at step (b1) if said step (b1) is carried out;
d1) putting said synthetic zeolite material in an aqueous solution comprising at least one source of an alkali metal M' and at least one source of metal M, wherein both sources of M and M' are fully soluble in water and wherein the molar ratio M'/M in the aqueous solution containing M and M' is of at least 1 and the weight ratio of said synthetic zeolite material over said aqueous solution containing M and M' is of at most 1000;
e1) optionally, stirring the solution obtained at step (d1) for at least 30 min;
f1) heating the solution for at least 12 h at a temperature of at least 50° C.;
g1) separating the solid obtained from said liquid obtained at step (f1);
h1) drying the solid obtained at step (g1) and calcining it at a temperature of at least 200° C. for at least 1 h and recovering said catalyst.

15. The process according to claim 14, characterized in that said at least one source of an alkali metal M' is selected from Li, Na, K, or Cs.

16. The process according to claim 15, characterized in that said at least one source of an alkali metal M' and said at least one source of metal M originate from two different compounds.

17. The process according to claim 16, characterized in that said at least one source of metal M is a salt soluble together with said at least one source of an alkali metal M' in water.

18. The process according to claim 15, characterized in that said at least one source of an alkali metal M' and said at least one source of metal M originate from the same compound.

19. The process according to claim 18, characterized in that said at least one source of an alkali metal M' and said at least one source of metal M is a sodium or a potassium salt of the metal M.

20. The process according to claim 18, characterized in that said at least one source of an alkali metal M' and said at least one source of metal M originate from $NaVO_3$, $KVO_3$, $Na_2MoO_4 \cdot 2H_2O$, or $K_2MoO_4$.

* * * * *

UNITED STATES PATENT AND TRADEMARK OFFICE
CERTIFICATE OF CORRECTION

PATENT NO. : 11,498,890 B1
APPLICATION NO. : 17/770188
DATED : November 15, 2022
INVENTOR(S) : Dubray et al.

It is certified that error appears in the above-identified patent and that said Letters Patent is hereby corrected as shown below:

In the Claims

Claim 1, Column 39, Line 29:
"at a temperature ranging from 8000 to 1100° C."

Should read:
"at a temperature ranging from 800 to 1100° C."

Signed and Sealed this
Third Day of January, 2023

Katherine Kelly Vidal
*Director of the United States Patent and Trademark Office*